(12) United States Patent
Zwiebel et al.

(10) Patent No.: US 10,091,997 B2
(45) Date of Patent: *Oct. 9, 2018

(54) COMPOSITION FOR INHIBITION OF INSECT HOST SENSING

(71) Applicant: Vanderbilt University, Nashville, TN (US)

(72) Inventors: Laurence Zwiebel, Nashville, TN (US); Gregory M. Pask, Nashville, TN (US); David Rinker, Nashville, TN (US); Patrick L. Jones, Danvers, MA (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/093,593

(22) Filed: Apr. 7, 2016

(65) Prior Publication Data

US 2016/0286807 A1 Oct. 6, 2016

Related U.S. Application Data

(63) Continuation of application No. 13/881,638, filed as application No. PCT/US2011/057246 on Oct. 21, 2011, now Pat. No. 9,332,757.

(60) Provisional application No. 61/406,786, filed on Oct. 26, 2010, provisional application No. 61/406,368, filed on Oct. 25, 2010.

(51) Int. Cl.
| | |
|---|---|
| *A01N 43/653* | (2006.01) |
| *A01M 1/20* | (2006.01) |
| *A01M 7/00* | (2006.01) |
| *A01N 25/12* | (2006.01) |
| *A01N 61/00* | (2006.01) |

(52) U.S. Cl.
CPC ......... *A01N 43/653* (2013.01); *A01M 1/2005* (2013.01); *A01M 1/2016* (2013.01); *A01M 7/0003* (2013.01); *A01N 25/12* (2013.01); *A01N 61/00* (2013.01); *A01M 2200/012* (2013.01)

(58) Field of Classification Search
None
See application file for complete search history.

(56) References Cited

U.S. PATENT DOCUMENTS

| | | | |
|---|---|---|---|
| 2,798,053 A | 7/1957 | Brown | |
| 3,755,560 A | 8/1973 | Dickert et al. | |
| 4,418,534 A | 12/1983 | Dufft | |
| 4,421,769 A | 12/1983 | Dixon et al. | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,011,681 A | 4/1991 | Ciotti et al. | |
| 5,087,445 A | 2/1992 | Haffey et al. | |
| 5,100,660 A | 3/1992 | Hawe et al. | |
| 5,567,430 A | 10/1996 | Levy | |
| 5,698,210 A | 12/1997 | Levy | |
| 5,824,328 A | 10/1998 | Levy | |
| 5,846,553 A | 12/1998 | Levy | |
| 5,858,384 A | 1/1999 | Levy | |
| 5,858,386 A | 1/1999 | Levy | |
| 5,885,605 A | 3/1999 | Levy | |
| 5,902,596 A | 5/1999 | Levy | |
| 5,939,462 A | 8/1999 | Connell et al. | |
| 5,983,390 A | 11/1999 | Desy | |
| 6,001,382 A | 12/1999 | Levy | |
| 6,335,027 B1 | 1/2002 | Levy | |
| 6,337,078 B1 | 1/2002 | Levy | |
| 6,346,262 B1 | 2/2002 | Levy | |
| 6,350,461 B1 | 2/2002 | Levy | |
| 6,387,386 B1 | 5/2002 | Levy | |
| 6,391,328 B1 | 5/2002 | Levy | |
| 6,663,838 B1 | 12/2003 | Soller et al. | |
| 7,090,147 B2 | 8/2006 | Lovett | |
| 7,306,167 B2 | 12/2007 | Colarusso et al. | |
| 7,314,723 B2 | 1/2008 | Zwiebel | |
| 9,332,757 B2 * | 5/2016 | Zwiebel | A01N 43/653 |
| 9,578,881 B2 | 2/2017 | Zwiebel et al. | |
| 2003/0165879 A1 | 9/2003 | Woods et al. | |
| 2003/0166850 A1 | 9/2003 | Jones et al. | |
| 2006/0260183 A1 | 11/2006 | Hockaday | |
| 2007/0160637 A1 | 7/2007 | Schilling | |
| 2008/0095813 A1 | 4/2008 | Kiec | |
| 2009/0099135 A1 | 4/2009 | Enan | |
| 2009/0136968 A1 | 5/2009 | Sallman | |

(Continued)

FOREIGN PATENT DOCUMENTS

| | | |
|---|---|---|
| AU | 2012254032 | 4/2012 |
| AU | 2012254032 A1 | 11/2013 |

(Continued)

OTHER PUBLICATIONS

U.S. Appl. No. 61/406,368, filed Oct. 25, 2010, Laurence Zwiebel (Vanderbilt University).
U.S. Appl. No. 61/406,786, filed Oct. 26, 2010, Laurence Zwiebel (Vanderbilt University).
U.S. Appl. No. 61/483,440, filed May 6, 2011, Laurence Zwiebel (Vanderbilt University).
U.S. Appl. No. 61/483,857, filed May 9, 2011, Laurence Zwiebel (Vanderbilt University).
U.S. Appl. No. 61/540,929, filed Sep. 29, 2011, Laurence Zwiebel (Vanderbilt University).
U.S. Appl. No. 61/586,492, filed Jan. 13, 2012, Laurence Zwiebel (Vanderbilt University).

(Continued)

*Primary Examiner* — Kortney L. Klinkel
*Assistant Examiner* — William Y Lee
(74) *Attorney, Agent, or Firm* — Ballard Spahr LLP

(57) ABSTRACT

The present invention provide chemical modulators of insect olfactory receptors. In particular, compounds and compositions are provided that can inhibit host targeting functions in insects such as mosquitos. Method of employing such agents, and articles incorporating the same, are also provided.

20 Claims, 9 Drawing Sheets

(56) References Cited

U.S. PATENT DOCUMENTS

| | | |
|---|---|---|
| 2009/0163545 A1 | 6/2009 | Goldfarb |
| 2009/0226422 A1 | 9/2009 | Chaudhary et al. |
| 2009/0253763 A1 | 10/2009 | Ohshita et al. |
| 2010/0226949 A1 | 9/2010 | Ray et al. |
| 2011/0139894 A1 | 6/2011 | Masterson et al. |
| 2011/0257211 A1 | 10/2011 | Chand et al. |
| 2012/0082639 A1 | 4/2012 | Hassanali et al. |
| 2014/0045690 A1 | 2/2014 | Defieber et al. |
| 2014/0242135 A1 | 8/2014 | Zwiebel et al. |

FOREIGN PATENT DOCUMENTS

| | | |
|---|---|---|
| CA | 2835328 | 4/2012 |
| CA | 2835328 A1 | 11/2012 |
| CN | 1030298 A | 1/1989 |
| CN | 101616914 A | 12/2009 |
| CN | 201180062303.0 | 10/2011 |
| CN | 2015106834069 | 10/2015 |
| CN | 103402988 B | 11/2015 |
| EP | 11838461.9 | 10/2011 |
| EP | 1278194.6 | 4/2012 |
| EP | 2632257 A2 | 9/2013 |
| EP | 2704575 A2 | 3/2014 |
| KR | 20080105463 | 12/2008 |
| WO | WO-1995/017091 A1 | 6/1995 |
| WO | WO-1998/035944 A1 | 8/1998 |
| WO | WO-00/35285 | 6/2000 |
| WO | WO-02/43483 | 6/2002 |
| WO | WO-2004/001058 A2 | 12/2003 |
| WO | WO-2004/030611 A2 | 4/2004 |
| WO | WO-2004/041209 A2 | 5/2004 |
| WO | WO-2004/089367 A1 | 10/2004 |
| WO | WO-2004/089416 A2 | 10/2004 |
| WO | WO-2005/087750 A1 | 9/2005 |
| WO | WO-2006/076009 A2 | 7/2006 |
| WO | WO-2006/131230 A2 | 12/2006 |
| WO | WO-2007/121512 A1 | 11/2007 |
| WO | WO-2009/030996 A1 | 3/2009 |
| WO | WO-2009/051801 A2 | 4/2009 |
| WO | WO-2009/086303 A2 | 7/2009 |
| WO | WO-2009/0232918 | 9/2009 |
| WO | WO-2010/003877 A1 | 1/2010 |
| WO | WO-2010/060151 A1 | 6/2010 |
| WO | PCT/US2011/057246 | 10/2011 |
| WO | WO-2011/163198 A2 | 12/2011 |
| WO | PCT/US2012/034847 | 4/2012 |
| WO | WO-2012/061039 A2 | 5/2012 |
| WO | WO-2012/154403 A2 | 11/2012 |
| WO | PCT/US2016/024076 | 3/2016 |
| WO | PCT/US2016/041918 | 7/2016 |
| ZA | 2013/09154 | 4/2012 |
| ZA | 2013/09154 | 11/2012 |

OTHER PUBLICATIONS

U.S. Appl. No. 13/881,638 (U.S. Pat. No. 9,332,757), filed Oct. 16, 2013 (Feb. 6, 2014), Laurence Zwiebel (Vanderbilt University).
U.S. Appl. No. 61/625,602, filed Apr. 17, 2012, Laurence Zwiebel (Vanderbilt University).
U.S. Appl. No. 14/115,553 (US 2014-0242135 A1), filed May 2, 2014 (Aug. 28, 2014) Laurence Zwiebel (Vanderbilt University).
U.S. Appl. No. 62/191,960, filed Jul. 13, 2015, Zwiebel (Vanderbilt Univ.).
U.S. Appl. No. 62/138,348, filed Mar. 25, 2015, Zwiebel (Vanderbilt Univ.).
International Search Report and Written Opinion dated Sep. 27, 2016 by the International Bureau for PCT/US16/41918, filed on Jul. 12, 2016 (Applicant—Vanderbilt University; Inventors—Zwiewel et al.) (6 pages).
Second Examination Report dated Jan. 20, 2017 by the Australian Patent Office for AU Application No. 2012254032, which was filed on Apr. 25, 2012 (Applicant—Vanderbilt University) (14 pages).
CAS Registry No. 1289917-54-9; May 4, 2011.
CAS Registry No. 333786-87-1; May 1, 2001.
Soliman, L. N. et al., "Synthesis of some substituted mercaptotriazoles with possible anticonvulsant and monoamine oxidase inhibiting activities", Bulletin of the Faculty of Pharmacy (Cairo University), 1990, vol. 28, No. 2, pp. 53-58.
First Office Action dated Mar. 1, 2017 by the SIPO for CN Application No. 2015106834069, which was filed on Oct. 20, 2015 and published as CN105394046 on Mar. 16, 2016 (Applicant—Vanderbilt University) (Original—6 pages// Translated—7 pages).
Acree et al., L-Lactic Acid: A Mosquito Attractant Isolated from Humans, Science, 161:1346-1347, 1968.
Antonny et al., The mechanism of aluminum-independent G-protein activation by fluoride and magnesium. 31P NMR spectroscopy and fluorescence kinetic studies, J. Bioi. Chem., 268:2393-2402, 1993.
Baumann et al., Primary structure and functional expression of a *Drosophila* cyclic nucleotide-gated channel presentin eyes and antennae., Embo. J., 13:5040-5050, 1994.
Benton et al., Variant ionotropic glutamate receptors as chemosensoryreceptors in *Drosophila*, Cell, 136:149-162, 2009.
Benton et al., Atypical membrane topologyand heteromeric function of *Drosophila* odorant receptors in vivo, PLoS Biol., 4:e20, 2006.
Bernier et al., Analysis of human skin emanations bygas chromatography/mass spectrometry. 1. Thermal desorption of attractants for the yellow fever mosquito (*Aedes aegypti*) from handled glass beads, Anal. Chern., 71:1-7, 1999.
Boekhoff et al., Pheromone-induced stimulation of inositol-trisphosphate formation in insect antennae is mediated byG-proteins, J. Comparative Physiol. B, 160:99-103, 1990.
Bohbotet al., Molecular characterization of the Aedes aegypti odorant receptor gene family, Insect. Mol. Biol., 16:525-537, 2007.
Brady et al., The role of body odours in the relative attractiveness of different men to malarial vectors in Burkina Faso,Ann. Trop. Med. Parasitol., 91:S121-122, 1997.
Breer et al., Rapid kinetics of second messenger formation in olfactorytransduction, Nature, 345:65-68, 1990.
Carnevale et al., [The aggressiveness of Anopheles gambiae A in relation to the age and sex of the human subjects], Bull. World Health Organ., 56:147-154, 1978.
Clyne et al., The odor specificities of a subset of olfactory receptor neurons are governed by Acj6, a POU-domain transcription factor, Neuron., 22:327-338,1999.
Clyne et al., Candidate taste receptors in *Drosophila*, Science, 287:1830-1834, 2000.
Cork and Park, Identification of electrophysiologically-active compounds for the malaria mosquito, *Anopheles gambiae*, in human sweat extracts, Med. Vet. Entomol., 10:269-276, 1996.
CTFA Cosmetic IngredientHandbook, vol. 3, p. 3187-3192.
Curtis, Fact and fiction in mosquito attraction and repulsion, Parasitology Today, 11:316-318, 1986.
Database Registry [online] Chemical Abstracts Service, Columbus, Ohio, US; Jun. 5, 2003 (Jun. 5, 2003) & Database Chemcats [Online] Chemical Abstracts Service, Columbus, US; Apr. 21, 2014 (Apr. 21, 2014), Database accession No. 0089984228.
DeJong and Knols, Olfactory responses of host-seeking Anopheles gambiae s.s. Giles (Diptera: Culicidae), Acta Trop., 59:333-335, 1995.
DeJong and Knols, Selection of biting sites on man by two malaria mosquito species, Experientia, 51:80-84, 1995.
Dekker et al., Innate preference for host-odour blends modulates degree of anthropophagy of; Anopheles gambiae sensu lato (Diptera: Culicidae), J. Med. Entomol., 38:868-871,2001a.
Dekker et al., Structure of host-odour plumes influences catch of Anopheles gambiae s.s. and Aedes aegypti in a dual-choice olfactometer, Physiol. Entomol.,26:124-134,2001b.
Dobritsa et al., Integrating the molecular and cellular basis of odor coding in the *Drosophila* antenna, Neuron., 37:827-841, 2003.
Eiras and Jepson, Host location byAedes aegypti (Diptera: Culicidae): a wind tunnel study of chemical cues, Bull. Entomol. Res., 81:151-160, 1991.
Elmore and Smith, Putative *Drosophila* odor receptor OR43b localizes to dendrites of olfactory neurons, Insect Biochem. Mol. Biol., 31:791-798,2001.

(56) References Cited

OTHER PUBLICATIONS

Engsontia et al., The red flour beetle's large nose: an expanded odorant receptor gene family in Tribolium castaneum, Insect Biochem. Mol. Biol., 38:387-397,2008.

Fox et al., Candidate odorant receptors from the malaria vector mosquito *Anopheles gambiae* and evidence of down-regulation in response to blood feeding, Proc. Natl. Acad. Sci. USA, 98:14693-14697, 2001.

Gao and Chess, Identification of candidate *Drosophila* olfactory receptors from genomic DNA sequence, Genomics, 60:31-39, 1999.

Gilles, The role of carbon dioxide in host-finding bymosquitoes (Diptera: Culicidae): a review, Bull. Entomol. Res., 70:525-532, 1980.

Goldman et al., Coexpression of two functional odor receptors in one neuron, Neuron., 45:661-666, 2005.

Hallem and Carlson, Cell, Coding ofOdors by a Receptor-Repertoire, 125:143-160, 2006.

Hallem et al., The Molecular Basis of Odor Coding in the *Drosophila* Antenna, Cell, 117:965-979, 2004a.

Hallem et al., Olfaction: mosquito receptor for human-sweat odorant, Nature, 427:212-213, 2004b.

Hildebrand and Shepherd, Mechanisms of olfactory discrimination: converging evidence for common principles across phyla., Annu. Rev. Neurosci., 20:595-631, 1997.

Hill et al., G protein-coupled receptors in Anopheles gambiae, Science, 298:176-178, 2002.

Holt et al., The genome sequence of the malaria mosquito *Anopheles gambiae*, Science, 298: 129-149, 2002.

Jones PL, et al., Functional agonism of insect odorant receptor ion channels, Proc Natl Acad Sci, 108(21): 8821-8825, 2011.

Jones et al., Functional conservation of an insect odorant receptor gene across 250 million years of evolution, Curr. Biol., 15:R119-R121,2005.

Jones et al., Two chemosensoryreceptors together mediate carbon dioxide detection in *Drosophila*, Nature, 445:86-90, 2007.

Kellogg, Water vapour and carbon dioxide receptors in Aedes aegypt, J Insect. Physiol., 16:99-108, 1970.

Kim et al., Identification of novel multi-trans membrane proteins from genomic databases using quasi-periodic structural properties, Bioinformatics, 16:767-775, 2000.

Krieger and Breer, Olfactory reception in invertebrates, Science, 286:720-723, 1999.

Krieger et al., A divergent gene family encoding candidate olfactory receptors ofthe moth *Heliothis virescens*, Eur. J Neurosci., 16:619-628, 2002.

Krieger et al., Identification of a cyclic nucleotide- and voltage-activated ion channel from insect antennae, Insect. Biochem. Mol. Biol., 29:255-267, 1999.

Kriegeret al., A candidate olfactory receptor subtype highly conserved across different insect orders, J. Comp. Physiol. A Neuroethol. Sens. Neural. Behav. Physiol., 189:519-526, 2003.

Krotoszynski et al., Characterization of human expired air: a promising investigative and diagnostic technique, J Chromatographic Sci., 15:239-244, 1977.

Kwon et al., The molecular basis of CO2 reception in *Drosophila*, Proc. Natl. Acad. Sci. USA, 104:3574-3578, 2007.

Labows Jr., Human odors—what can they tell us? Perfumer & Flavorist, 4:12-17, 1979.

Larsson et al., Or83b Encodes a Broadly Expressed Odorant Receptor Expressed Odorant Receptor Essential for *Drosophila* Olfaction, Neuron., 43:703-714, 2004.

Laue et al., G-protein activation, identification and immunolocalization in pheromone sensitive sensilla trichodea of moth, Cell Tissue Res., 288:149-158, 1997.

Lindsayet al., Variation in attractiveness of human subjects to malaria mosquitoes (Diptera: Culicidae) in The Gambia, J Med. Entomol., 30:308-373, 1993.

Lu et al., Odor Coding in the Maxillary Palp of the Malaria Vector Mosquito *Anopheles gambiae*, Curr. Biol., 17:1533-1544, 2007.

Liu et al., Distinct Olfactory Signaling Mechanisms in the Malaria Vector Mosquito *Anopheles gambiae*, PLoS Biology8(8): e1000467, 2010.

Lundin et al., Membrane topology of the *Drosophila* OR83b odorant receptor, FEBS Lett., 581(29):5601-5604, 2007.

Mboera and Takken, Carbon dioxide chemotropism in mosquitoes (Diptera: Culicidae) and its potential in vector surveillance and management programmes, Rev. Med. Vet. Entomol., 85:355-368, 1997.

McCutcheon's, Detergents and Emulsifiers, North American Edition, 1986.

Meijerink and van Loon, Sensitivities of antennal olfactory neurons of the malaria mosquito, *Anopheles gambiae*,to carboxylic acids, J Insect Physiol., 45:365-373, 1999.

Meijerink et al., Olfactory receptors on the antennae of the malaria mosquito *Anopheles gambiae* are sensitive to ammonia and other sweat-borne components, J. InsectPhysiol., 47:455-464, 2001.

Merrill et al., Molecular characterization of arrestin familymembers in the malaria vector mosquito, *Anopheles gambiae*, Insect Molecul. Biol., 12:641-650, 2003.

Merrill et al., Odorant-specific requirements for arrestin function in *Drosophila* olfaction, J Neurobiol., 63:15-28, 2005.

Merrill et al., Visual arrestins in olfactory pathways of *Drosophila* and the malaria vector mosquito *Anopheles gambiae*, Proc. Natl. Acad. Sci. USA, 99:1633-1638, 2002.

Mombaerts, Molecular biology of odorant receptors in vertebrates, Annu. Rev. Neurosci., 22:487-509, 1999.

Muirhead-Thomson, Low Gametocyte Thresholds of Infection of Anopheles with Plasmodium Falciparum, Brit. Med. J., I: 1114-1117, 1951.

Pelosi and Maida, Odorant-binding proteins in insects, Comp. Biochem. Physiol. B Biochem. Mol. Biol., 111:503-514, 1995.

Pitts et al., A highly conserved candidate chemoreceptor expressed in both olfactory and gustatory tissues in the malaria vector Anopheles gambiae, Proc. Natl. Acad. Sci. USA, 101:5058-5063, 2004.

Qiu et al., Olfactory Coding in Antennal Neurons of the Malaria Mosquito, *Anopheles gambiae*, Chem. Senses, 31:845-863, 2006b.

Qiu et al., Attractiveness of MM-X Traps Baited with Human or Synthetic, Odor to Mosquitoes (Diptera: Culicidae) in The GambiaMed. Vet. Entomol., 20:280-287, 2006a.

Robertson and Wanner, Expansion of the odorant, but not gustatory, receptor family, The chemoreceptor superfamily in the honey bee, Apis mellifera:Genome Res., 16:1395-1403,2006.

Robertson et al., Molecular evolution of the insect chemoreceptor gene superfamilyin *Drosophila melanogaster*, Proc. Natl. Acad. Sci. USA, 100(2):14537-14542, 2003.

Rutzler et al., Ga Encoding Gene Family of the Malaria Vector Mosquito *Anopheles gambiae*: Expression Analysis and Immunolocalization of AGaq and AGao in Female Antennae, J Cornp. Neural., 499:533-545, 2006.

Sato et al., Insect olfactory receptors are heteromeric ligand-gated ion channels, Nature, 452(7190): 1002-1006, 2008.

Schreck et al., Mosquito attraction to substances from the skin of different humansJ. Am. Mosq. Control Assoc., 6:406-410, 1990.

Scott et al., A chemosensorygene family encoding candidate gustatory and olfactory receptors in *Drosophila*, Cell, 104:661-673, 2001.

Smith, *Drosophila* odor receptors revealed, Neuron., 22:203-204, 1999.

Stengl, Inositol-trisphosphate-dependent calcium currents precede cation currents in insect olfactory receptor neurons in vitro, J Comp. Physiol. [A], 174:187-194, 1994.

Storkuhl and Kettler, Functional analysis of an olfactory receptor in *Drosophila melanogaster*, Proc. Natl. Acad. Sci. USA, 98:9381-9385, 2001.

Suh et al., Light Activation of an Innate Olfactory Avoidance Response in *Drosophila*, Curr. Biol., 17:905-908, 2007.

Takken and Knols, Odor-mediated behavior ofAfrotropical malaria mosquitoes, Annu. Rev. Entomol., 44:131-157, 1999.

Takken et al., Odor-mediated flight behavior ofAnopheles gambiae gilesSensu Stricto andAn. stephens i liston in response to CO2, acetone, and 1-octen-3-ol (Diptera: Culicidae), J Insect Behavior, 10:395-407, 1997.

(56) References Cited

OTHER PUBLICATIONS

Takken, The role of olfaction in host-seeking of mosquitoes: a review, Insect Sci. Applns., 12:287-295, 1991.
Thomas, TCE: Biting activity of Anopheles gambiae, Brit. Med. J., 2:1402, 1951.
Vosshall et al., An olfactory sensorymap in the fly brain, Cell, 102:147-159, 2000.
Vosshall et al., A spatial map of the olfactory receptor expression in the *Drosophila* antenna, Cell, 96:725-736, 1999.
Vosshall, The molecular logic of olfaction in *Drosophila*, Chem. Senses, 26:207-213, 2001.
Wetzel et al., Functional expression and characterization of a *Drosophila* odorant receptor in a heterologous cell system, Proc. Natl. Acad. Sci. USA, 98:9377-9380,2001.
Wicher et al., *Drosophila* odorant receptors are both ligand-gated and cyclicnucleotide-activated cation channels, Nature, 452(7190)1007-1011, 2008.
Wistrand et al., A general model of G protein-coupled receptor sequences and its application to detect remote homologs, Protein Sci., 15:509-521, 2006.
Xia et al., The molecular and cellular basis of olfactory-driven behavior in Anopheles gambiae larvae, Proc. Natl. Acad. Sci. USA, 105:6433-6438, 2008.
Zwiebel and Takken, Olfactory regulation of mosquito-host interactions, Insect Biochem. Molec. Biol., 34:645-652, 2004.
Vosshall et al., A unified nomenclature system for the insect olfactory coreceptor, Chemical Senses Advanced Access, Mar. 25, 2011.
Lee. S. H. et al, Preparation of triazole derivatives as T-type calcium channel blockers, CAS accession No. 150: 77688.
Database Registry [online] Chemical Abstracts Service, Columbus, Ohio, US; Jun. 5, 2003 (Jun. 5, 2003) Database accession No. 525582-84-7/RN.
Database Registry [online] Chemical Abstracts Service, Columbus, Ohio, US; Feb. 21, 2014 (Feb. 21, 2014) Database accession No. 0089984228.
Bohlen et al., A bivalent tarantula toxin activates the capsaicin receptor, TRPV1, by targeting the outer pore domain, Cell, 141: 834-84S,2010.
Caterina et al., The capsaicin receptor: a heat-activated ion channel in the pain pathway, Nature, 389: 816-824, 1997.
International Preliminary Report on Patentability issued by the International Bureau dated Apr. 30, 2013 for PCT/US2011/057246 filed Oct. 21, 2011 and published as WO 2012/061039 on May 10, 2012 (Applicant—Vanderbilt University; Inventors—Zwiewel et al.) (7 pages).
International Search Report mailed by the International Bureau dated Jun. 21, 2012 for PCT/US2011/057246 filed Oct. 21, 2011 and published as WO 2012/061039 on May 10, 2012 (Applicant—Vanderbilt University; Inventors—Zwiewel et al.) (5 pages).
Written Opinion mailed by the International Bureau dated Jun. 21, 2012 for PCT/US2011/057246 filed Oct. 21, 2011 and published as WO 2012/061039 on May 10, 2012 (Applicant—Vanderbilt University; Inventors—Zwiewel et al.) (6 pages).
Extended European Search Report issued by the European Patent Office dated May 28, 2014 for Application No. 11838461.9 filed Oct. 21, 2011 and published as EP 2632257 on Sep. 4, 2013 (Applicant—Vanderbilt University; Inventors—Zwiebel et al.) (9 pages).
Preliminary Amendment dated Apr. 7, 2016 to the U.S. Patent and Trademark Office for U.S. Appl. No. 15/093,593, filed Apr. 7, 2016 (Inventor—Laurence Zwiebel et al; Applicant—Vanderbilt University) (3 Pages).
Preliminary Amendment dated Apr. 25, 2013 to the U.S. Patent and Trademark Office for US Application No. PCT/US2011/057246 which was filed on Oct. 21, 2011 (Inventor—Laurence Zwiebel et al; Applicant—Vanderbilt University) (6 Pages).
Requirement for Restriction/Election dated Jun. 9, 2014 by the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (12 Pages).
Response to Restriction Requirement dated Aug. 8, 2014 to the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (7 Pages).
Non Final Rejection dated Dec. 15, 2014 by the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (21 Pages).
Response to Non Final Rejection dated Mar. 16, 2015 to the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (13 Pages).
Response to Ex Parte Quayle Action was mailed on Sep. 25, 2015 to the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (13 Pages).
Notice of Allowance dated Jan. 12, 2016 by the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (7 Pages).
Issue Notification dated Apr. 20, 2016 by the U.S. Patent and Trademark Office for U.S. Appl. No. 13/881,638, filed Oct. 16, 2013 and published as US 2014-0039013 A1 on Feb. 6, 2014 (Inventor—Laurence Zwiebel et al; Applicant—Vanderbilt University) (1 Page).
First Office Action dated Jun. 26, 2014 by the State Intellectual Property Office of China for Chinese Application No. 201180062303.0 which was filed on Oct. 21, 2011 and published as CN103402988A on Nov. 20, 2013 (Inventor—Laurence Zwiebel et al; Applicant—Vanderbilt University) (8 Pages).
Second Office Action dated Apr. 16, 2015 bythe State Intellectual Property Office of China for Chinese Application No. 201180062303.0 which was filed on Oct. 21, 2011 and published as CN103402988A on Nov. 20, 2013 (Inventor—Laurence Zwiebel et al; Applicant—Vanderbilt University) (8 Pages).
Notification of Grant dated Nov. 25, 2015 by the State Intellectual Property Office of China for Chinese Application No. 201180062303.0 which was filed on Oct. 21, 2011 and published as CN103402988A on Nov. 20, 2013 (Inventor—Laurence Zwiebel et al; Applicant—Vanderbilt University) (8 Pages).
Preliminary Amendment dated Nov. 4, 2013 to the U.S. Patent and Trademark Office for U.S. Appl. No. PCT/US2012/034847, which was filed Apr. 25, 2012 and published as WO2012/154403 on Nov. 15, 2012 (Inventor—Laurence Zwiebel et al; Applicant—Vanderbilt University) (17 Pages).
Requirement for Restriction/Election dated Jul. 6, 2015 by the U.S. Patent and Trademark Office for U.S. Appl. No. 14/115,553, filed May 2, 2014 and published as US 2014-0242135 A1 on Feb. 6, 2014 (Inventor—Laurence Zwiebel et al; Applicant—Vanderbilt University) (10 Pages).
Response to Restriction Requirement dated Sep. 8, 2015 to the U.S. Patent and Trademark Office for U.S. Appl. No. 14/115,553, filed May 2, 2014 and published as US 2014-0242135 A1 on Feb. 6, 2014 (Inventor—Laurence Zwiebel et al; Applicant—Vanderbilt University) (15 Pages).
Non Final Rejection dated Dec. 17, 2015 by the U.S. Patent and Trademark Office for U.S. Appl. No. 14/115,553, filed May 2, 2014 and published as US 2014-0242135 A1 on Feb. 6, 2014 (Inventor—Laurence Zwiebel et al; Applicant—Vanderbilt University) (10 Pages).
Response to Non Final Rejection dated Apr. 18, 2016 to the U.S. Patent and Trademark Office for U.S. Appl. No. 14/115,553, filed May 2, 2014 and published as US2014-0242135 A1 on Feb. 6, 2014 (Inventor—Laurence Zwiebel et al; Applicant—Vanderbilt University) (10 Pages).
Final Rejection dated Jun. 16, 2016 by the U.S. Patent and Trademark Office for U.S. Appl. No. 14/115,553, filed May 2, 2014 and

(56) References Cited

OTHER PUBLICATIONS published as US 2014-0242135 A1 on Feb. 6, 2014 (Inventor—Laurence Zwiebel et al; Applicant—Vanderbilt University) (10 Pages).
Supplementary European Search Report issued by the European Patent Office dated May 13, 2015 for European Application No. 1278194.6 filed Apr. 25, 2012 and published as EP 2704575 on Mar. 12, 2014 (Applicant—Vanderbilt University; Inventors—Laurence Zwiebel et al.) (8Pages).
International Preliminary Report on Patentability issued by the International Bureau dated Mar. 25, 2014 for PCT/US2012/034847 filed Apr. 25, 2012 and published as WO 2012/154403 on Nov. 15, 2012 (Applicant—Vanderbilt University; Inventors—Laurence Zwiewel et al.) (8 pages).
International Search Report dated Sep. 17, 2012 by the International Bureau for PCT/US2012/034847 filed Apr. 25, 2012 and published as WO 2012/154403 on Nov. 15, 2012 (Applicant—Vanderbilt University; Inventors—Laurence Zwiewel et al.) (4 pages).
Written Opinion dated Sep. 17, 2012 by the International Bureau for PCT/US2012/034847 filed Apr. 25, 2012 and published as WO 2012/154403 on Nov. 15, 2012 (Applicant—Vanderbilt University; Inventors—Laurence Zwiewel et al.) (7 pages).
Examination Report dated Jan. 27, 2016 by the Australian Patent Office for Austrailian Application No. 2012254032 filed Apr. 25, 2012 (Applicant—Vanderbilt University; Inventors—Zwiewel et al.) (6 pages).
International Search Report and Written Opinion dated Jun. 20, 2016 by the International Bureau for PCT/US2016/24076, filed on Mar. 24, 2016 (Applicant—Vanderbilt University; Inventors—Zwiewel et al.) (13 pages).
Second Office Action dated Aug. 31, 2017 by the SIPO for CN Application No. 2015106834069, which was filed on Oct. 20, 2015 and published as CN 105394046 on Mar. 16, 2016 (Applicant—Vanderbilt University) (Original—4 pages// Translated—7 pages).
Communication pursuant to Article 94(3) issued by the European Patent Office dated Apr. 6, 2017 for Application No. 11838461.9 filed Oct. 21, 2011 and published as EP 2632257 on Sep. 4, 2013 (Applicant—Vanderbilt University; Inventors—Zwiebel et al.) (5 pages).
Second Examination Report dated Jan. 20, 2017 by the Australian Patent Office for Australian Application No. 2012254032 filed Apr. 25, 2012 and granted as AU 2012254032 on Jun. 8, 2017 (Applicant—Vanderbilt University; Inventors—Zwiebel et al.) (14 pages).
Notice of Acceptance dated Feb. 10, 2017 by the Australian Patent Office for Australian Application No. 2012254032 filed Apr. 25, 2012 and granted as AU 2012254032 on Jun. 8, 2017 (Applicant—Vanderbilt University; Inventors—Zwiebel et al.) (4 pages).
Certificate of Grant dated Jun. 8, 2017 by the Australian Patent Office for Australian Application No. 2012254032 filed Apr. 25, 2012 and granted as AU 2012254032 on Jun. 8, 2017 (Applicant—Vanderbilt University; Inventors—Zwiebel et al.) (1 page).
Response to Final Rejection dated Sep. 16, 2016 to the U.S. Patent and Trademark Office for U.S. Appl. No. 14/115,553, filed May 2, 2014 and granted as 9,578,881 on Feb. 28, 2017 (Inventor—Laurence Zwiebel et al; Applicant—Vanderbilt University) (17 Pages).
Notice of Allowance dated Oct. 7, 2016 by the U.S. Patent and Trademark Office for U.S. Appl. No. 14/115,553, filed May 2, 2014 and granted as 9,578,881 on Feb. 28, 2017 (Inventor—Laurence Zwiebel et al; Applicant—Vanderbilt University) (7 Pages).
Amendment after Notice of Allowance(Rule 312) dated Jan. 3, 2017 by the U.S. Patent and Trademark Office for U.S. Appl. No. 14/115,553, filed May 2, 2014 and granted as 9,578,881 on Feb. 28, 2017 (Inventor—Laurence Zwiebel et al; Applicant—Vanderbilt University) (119 Pages).
Response to Amendment Under Rule 312 dated Jan. 9, 2017 by the U.S. Patent and Trademark Office for U.S. Appl. No. 14/115,553, filed May 2, 2014 and granted as 9,578,881 on Feb. 28, 2017 (Inventor—Laurence Zwiebel et al; Applicant—Vanderbilt University) (2 Pages).
Issue Notification dated Feb. 8, 2017 by the U.S. Patent and Trademark Office for U.S. Appl. No. 14/115,553, filed May 2, 2014 and granted as 9,578,881 on Feb. 28, 2017 (Inventor—Laurence Zwiebel et al; Applicant—Vanderbilt University) (1 Page).
Database CA [online], Chemical Abstracts Service, Columbus, OH, US; Database Accession No. 117:111530 CA. Synthesis of Some Substituted Mercaptotriazoles with Possible Anticonvulsant and Monoamine Oxidase Inhibiting Activities. Soliman, L.N et al. Bulletin of the Faculty of Pharm. (Cairo Univ.). 1990; 28(2):53-8.
Jones, P.L. et al., Allosteric Antagonism of Insect Odorant Receptor Ion Channels. PLoS One. 2012; 7(1):e30304 (7 pages).
Micheli, F. et al., 2-Methyl-3-fuRanyl-4H-1,2,4-triazol-3-ylthioamides: A New class of Selective Orexin 2 Antagonists. Bioorg Med Chem Lett. 2010; 20(22):6405-7.
International Preliminary Report on Patentability dated Jan. 16, 2018 by the International Searching Authority for Patent Application No. PCT/US2016/041918, which was filed on Jul. 12, 2016 and published as WO 2017/011466 on Jan. 19, 2017 (Inventor—Zwiebel et al.; Applicant—Vanderbilt University) (5 pages).
Communication Pursuant to Article 94(3) EPC dated Jan. 26, 2018 by the European Patent Office for Patent Application No. 12781894.6, which was filed on Apr. 25, 2012 and published as EP 2704575 on Mar. 12, 2014 (Inventor—Zwiebel et al.; Applicant—Vanderbilt University) (8 pages).
Non-Final Office Action dated Feb. 7, 2018 by the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (10 pages).
CAS Registry No. 1290415-35-8; May 5, 2011.
CAS Registry No. 1290271-73-6; May 5, 2011.
CAS Registry No. 1289977-38-3; May 4, 2011.
CAS Registry No. 1289450-47-0; May 3, 2011.
CAS Registry No. 1287847-77-1; May 1, 2011.
CAS Registry No. 1278492-10-6; Apr. 11, 2011.
CAS Registry No. 1182613-44-0; Sep. 11, 2009.
CAS Registry No. 1181196-30-4; Sep. 8, 2009.
CAS Registry No. 848989-24-2; Apr. 22, 2005.
CAS Registry No. 442631-22-3; Aug. 6, 2002.
CAS Registry No. 440638-11-9; Jul. 29, 2002.
CAS Registry No. 423130-78-3; May 30, 2002.
CAS Registry No. 423130-74-9; May 30, 2002.
CAS Registry No. 412921-00-7; May 9, 2002.
CAS Registry No. 381682-23-1; Jan. 10, 2002.
CAS Registry No. 332385-30-5; Apr. 25, 2001.
CAS Registry No. 1286975-43-6; STN Entry Date Apr. 28, 2011.
CAS Registry No. 1286430-12-3; STN Entry Date Apr. 27, 2011.
CAS Registry No. 1209715-08-1; STN Entry Date Mar. 14, 2010.
CAS Registry No. 1180894-98-7; STN Entry Date Sep. 6, 2009.
CAS Registry No. 1091498-95-1; STN Entry Date Dec. 29, 2008.
CAS Registry No. 952921-55-0; STN Entry Date Nov. 11, 2007.
CAS Registry No. 948289-46-1; STN Entry Date Sep. 27, 2007.
CAS Registry No. 948210-77-3; STN Entry Date Sep. 27, 2007.
CAS Registry No. 880800-32-8; STN Entry Date Apr. 18, 2006.
CAS Registry No. 585550-72-7; STN Entry Date Sep. 15, 2003.

* cited by examiner

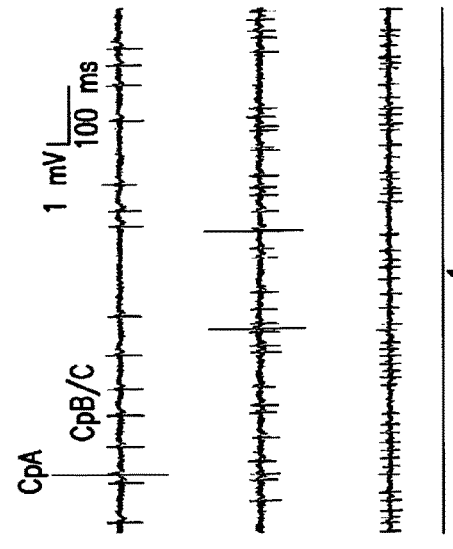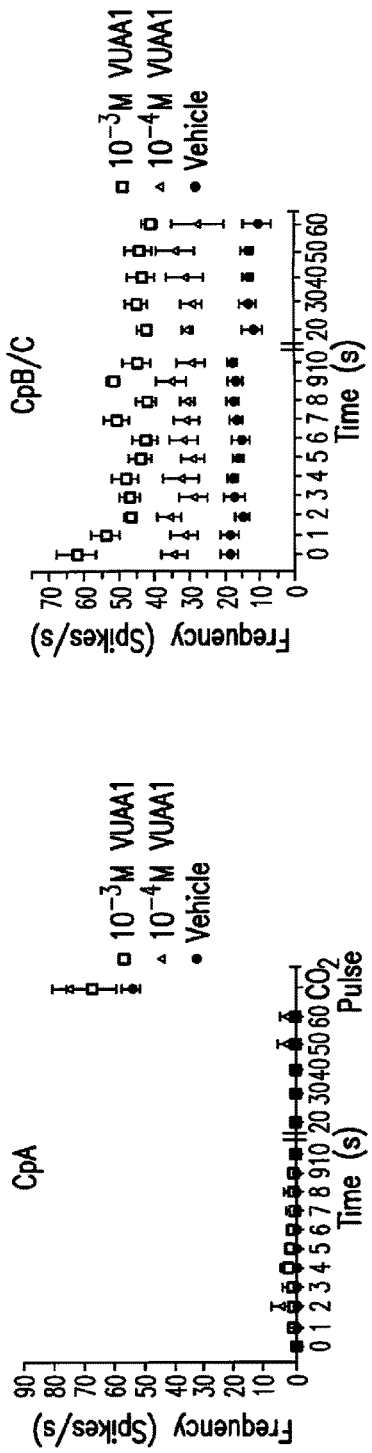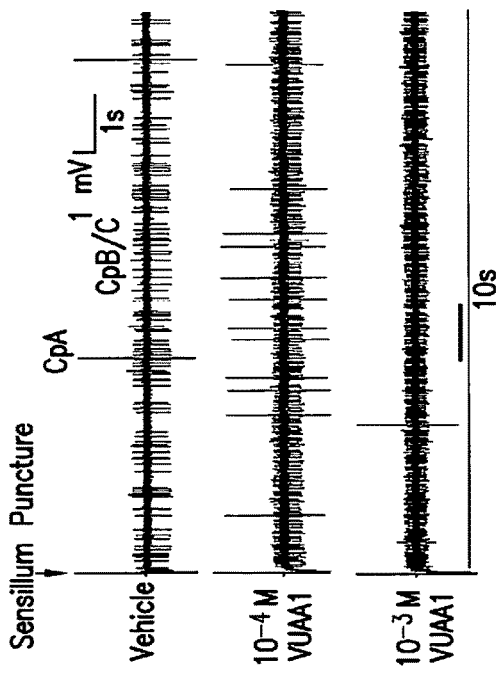

COMPOSITION FOR INHIBITION OF INSECT HOST SENSING

The present application is a Continuation Application of U.S. application Ser. No. 13/881,638, filed Oct. 16, 2013, which is a U.S. National Phase Application of International Application No. PCT/US11/57246, filed Oct. 21, 2011, which claims the benefit of U.S. Provisional Application No. 61/406,368, filed Oct. 25, 2010 and U.S. Provisional Application No. 61/406,786, filed Oct. 26, 2010, all of which applications are incorporated herein fully by this reference.

This application claims benefit of priority to U.S. Provisional Application Ser. No. 61/406,368, filed Oct. 25, 2010, and 61/406,786, filed Oct. 26, 2010, the entire contents of which are hereby incorporated by reference.

BACKGROUND OF THE INVENTION

I. Field of the Invention

The present invention relates to the fields of entomology and infectious disease. More particular, the invention relates to methods and compositions for disrupting host-targeting in mosquitoes and other insects.

II. Related Art

Insects acting as agricultural pests and disease vectors are responsible for extraordinary economic and medical impacts, respectively. Human malaria affects regions that are home to over two billion people, and cause at least one million deaths each year. The social and economic impact of the disease are staggering, with a disproportionate number of deaths coming in children aged 5 or less. And despite successes in limiting the disease in the last half of the previous century, recent trends show a resurgence in malarial infections in certain areas, and suggest a shift in modes of malarial transmission.

Currently the primary tool to prevent the spread of malaria is the use of insecticides that kill the mosquito vector. However, each of the various forms of insecticide treatment—residual house spraying, insecticide treated clothes, bedding and netting, and chemical larviciding—have drawbacks, including environmental and host toxicity, limited duration and need for insect contact. Biological larviciding can avoid toxicity issues, but takes time and is quite expensive. Chemoprophylaxis is also expensive and may have unacceptable side effects. Finally, segregating populations is expensive and in many cases (developing world countries) impractical.

Thus, while there are many different ways to attack malaria, and each have contributed substantially to limiting the spread of disease, they also each have limitations that leave room for substantial improvement.

SUMMARY OF THE INVENTION

Thus, in accordance with the present invention, there is provided a method of disrupting host-seeking behavior in an insect comprising providing to an insect environment a compound that binds to and/or agonizes, insect Orco ion channels (previously designated AgOR7 in *Anopheles gambiae*, but referred herein as equivalents). The insect may be a Culcine or Anphelin mosquito, a Dipteran, Lepidopteran or Ixodida insect. Other agricultural pest insects include Acalymma, *Acleris variegana*, African armyworm, Africanized bee, *Agromyzidae, Agrotis munda, Agrotis porphyricollis, Aleurocanthus woglumi, Aleyrodes proletella, Anasa tristis, Anisoplia austriaca, Anthonomus pomorum, Anthonomus signatus, Aonidiella aurantii*, Aphid, *Aphis fabae, Aphis gossypii*, Apple maggot, Argentine ant, Army cutworm, *Arotrophora arcuatalis, Asterolecanium coffeae*, Australian plague locust, *Bactericera cockerelli, Bactrocera, Bactrocera correcta, Bagrada hilaris*, Banded hickory borer, Banksia Boring Moth, Beet armyworm, Bogong moth, Boll weevil, *Brevicoryne brassicae*, Brown locust, Brown marmorated stink bug, Brown planthopper, Cabbage Moth, Cabbage worm, *Callosobruchus maculates*, Cane beetle, Carrot fly, *Cecidomyiidae, Ceratitis capitata*, Cereal leaf beetle, *Chlorops pumilionis, Citrus* long-horned beetle, *Coccus viridis*, Codling moth, Coffee borer beetle, Colorado potato beetle, Confused flour beetle, *Crambus*, Cucumber beetle, *Curculio nucum*, Dark Sword-grass, Date stone beetle, *Delia* (genus), *Delia antique, Delia floralis, Delia radicum*, Desert locust, *Diabrotica*, Diamondback moth, *Diaphania indica, Diaphania nitidalis, Diaphorina citri, Diaprepes abbreviates*, Differential grasshopper, *Dociostaurus maroccanus, Drosophila suzukii, Erionota thrax, Eriosomatinae, Eumetopina flavipes*, European Corn Borer, *Eurydema oleracea, Eurygaster integriceps*, Forest bug, *Frankliniella occidentalis, Fankliniella tritici, Galleria mellonella*, Garden Dart, Greenhouse whitefly, *Gryllotalpa orientalis, Gryllus pennsylvanicus*, Gpsy moths, *Helicoverpa armigera, Helicoverpa zea, Henosepilachna vigintioctopunctata*, Hessian fly, Japanese beetle, Khapra beetle, *Lampides boeticus*, Leaf miner, *Lepidiota consobrina, Lepidosaphes ulmi, Leptoglossus zonatus, Leptopterna dolabrata*, Lesser wax moth, *Leucoptera* (moth), *Leucoptera caffeine*, Light brown apple moth, *Lissorhoptrus oryzophilus*, Long-tailed Skipper, *Lygus* (genus), *Lygus hesperus, Maconellicoccus hirsutus, Macrodactylus subspinosus, Macrosiphum euphorbiae*, Maize weevil, *Manduca sexta, Mayetiola hordei*, Mealybug, *Megacopta cribraria*, Moth, Leek moth, *Myzus persicae, Nezara viridula*, Olive fruit fly, *Opomyzidae, Papilio demodocus, Paracoccus marginatus, Paratachardina pseudolobata*, Pea aphid, *Pentatomoidea, Phthorimaea operculella, Phyllophaga* (genus), *Phylloxera, Phylloxeroidea, Pieris brassicae*, Pink bollworm, *Platynota idaeusalis*, Plum curculio, *Pseudococcus viburni, Pyralis farinalis*, Red imported fire ant, Red locust, *Rhagoletis cerasi, Rhagoletis indifferens, Rhagoletis mendax, Rhopalosiphum maidis, Rhynchophorus ferrugineus, Rhyzopertha dominica*, Rice Moth, Russian wheat aphid, San Jose scale, *Sciaridae, Scirtothrips dorsalis, Scutelleridae*, Serpentine leaf miner, Silver Y, Silverleaf whitefly, Small hive beetle, Soybean aphid, *Spodoptera cilium, Spodoptera litura*, Spotted cucumber beetle, Squash vine borer, *Stenotus binotatus, Sternorrhyncha, Strauzia longipennis*, Striped flea beetle, Sunn pest, Sweetpotato bug, Tarnished plant bug, *Thrips* (genus), *Thrips palmi, Toxoptera citricida, Trioza erytreae, Tuta absoluta*, Varied carpet beetle, *Virachola Isocrates*, Waxworm, Western corn rootworm, Wheat fly, Wheat weevil, Winter Moth, and *Xyleborus glabratus*.

The method may comprise contacting a host surface located in said environment with said compound; may comprise aerosol or mist delivery to said environment; may comprise application to a water surface in said environment; may comprise application to a shelter or clothing surface in said environment; may comprise use of a shelter or article of clothing containing said compound in said environment; or may comprise depositing a solid form of said compound in said environment. The compound may be VUAA1. The method may further comprise provision of an insect repellent to said environment, such as a mosquito repellent.

In another embodiment, there is provided a container comprising a VUAA1 in a liquid or gaseous dispersion. The gaseous dispersion may be an aerosol. The container may further comprising a nozzle or valve, a porous applicator, or a rolling applicator.

In yet another embodiment, there is provided a fabric or material comprising VUAA1. The fabric or material may clothing, a shelter, bedding or netting.

In still another embodiment, there is provided a water soluble tablet comprising VUAA1. Further embodiments include:

methods of disrupting transmission of a mosquito-borne disease comprising providing to a mosquito environment a compound that binds to and/or agonizes a mosquito ORco ion channel, such as AgOR7;

methods of reducing mosquito bites comprising providing to a mosquito environment a compound that binds to and/or agonizes a mosquito ORco ion channel, such as AgOR7;

methods of reducing mosquito reproduction comprising providing to a mosquito environment a compound that binds to and/or agonizes a mosquito ORco ion channel, such as AgOR7;

methods of reducing mosquito infestation in an environment comprising providing to said environment a compound that binds to and/or agonizes a mosquito ORco ion channel, such as AgOR7;

methods of reducing crop damage by an insect population comprising providing to a crop-growing environment a compound that binds to and/or agonizes, an ORco ion channel; and a method of reducing infestation of a crop-damaging insect comprising providing to a crop-growing environment populated by a crop-damaging insect population a compound that binds to and/or agonizes, an ORco ion channel.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Structure of VUAA1. (FIG. 3B) Concentration response curves (CRCs) generated from Fluo-4 acetoxymethyl ester-based $Ca^{2+}$ imaging with AgORco and AgORco+AgOR10, cell lines in response to VUAA1. (FIGS. 3C-D) Whole-cell patch clamp recordings of concentration-dependent responses to VUAA1 in cells stably expressing AgORco alone and AgORco+AgOR10. (FIG. 3E) Benzaldehyde (BA), an AgOR10 agonist, elicits concentration-dependent responses to AgORco+AgOR10 cells. (FIG. 3F) Whole-cell current responses to VUAA1 in HEK293 cells expressing DmOR83b and HvOR2. Cells in FIGS. 3C, 3D, 3E, and 3F were clamped at −60 mV.

(FIGS. 4A-C), Representative traces of voltage-dependent currents in AgORco (FIG. 4A) and AgORco+AgOR10 (FIGS. 4B-C) cells. Holding potentials ranged from −60 mV to +40 mV in 20 mV increments. (FIG. 4D), Current-voltage relationships of (FIG. 4A) n=3, (FIG. 4B) n=7, and (FIG. 4C) n=4 from normalized peak currents.

(FIG. 5A) Single-channel recording from an outside-out excised patch pulled from an HEK293 cell-expressing AgORco7. (FIGS. 5B-D) Expansions of trace (FIG. 5A) before (FIG. 5B) during (FIG. 5C), and after (FIG. 5D) a 5 s application of −4.0 log M VUAA1. All-point current histograms of trace expansions are inset in FIGS. 5B-D. Excised membrane patch was held at −60 mV.

FIGS. 6A-D. VUAA1 activates AgORco-expressing neurons in *Anopheles gambiae* females. (FIG. 6A) Representative traces of SSR recordings from capitate peg sensilla upon electrode puncture. VUAA1 or vehicle alone (DMSO) was delivered through the glass recording electrode. CpA is discernible from the smaller CpB/C action potentials. Preparations were kept under a steady stream of humidified, synthetic air (21% $O_2$/79% $N_2$) to limit the basal activity of CpA. (FIG. 6B) Expansions of traces as in FIG. 3A. (FIG. 6C) Activity of CpA neuron in response to VUAA1. Spike frequency was calculated every second for the first 10 s after sensillum puncture and every 10 s thereafter. After 60 s, the preparation was pulsed for 2 s with atmospheric air to confirm a functional CpA neuron. Sensilla that did not respond to CO2 or 1-octen-3-ol were excluded from analysis. (FIG. 6D) Activity of CpB/CpC neurons in response to VUAA1 as in FIG. 6C.

(FIG. 7A) Histogram of normalized currents from concentration-dependent responses in FIGS. 7C-E (n=5). (FIG. 7B) Un-transfected HEK293 cells did not respond to either VUAA1 or BA (n=5). (FIG. 7C) GFP was co-transfected with DmOR83b or HvOR2 to identify cells expressing the OR. GFP alone cells had no currents from VUAA1 or BA (n=4). (FIGS. 7D-E) For comparison, AgORco and AgORco+AgOR10 cells both depolarized during VUAA1 application, while only AgORco+AgOR10 cells responded to BA. Holding potentials for all recordings were −60 mV. (FIG. 7F) VUAA1 did not elicit currents in cells stably expressing another cation channel, rat transient receptor potential vanilloid 1 (rTRPV1), but did respond to the agonist capsaicin.

(FIG. 8A) Representative trace of whole-cell recordings from cells expressing AgORco+AgOR10 with application of 8-Br-cAMP, 8-Br-cGMP, and BA (n=4). (FIG. 8B) Representative trace from AgORco cells with application of 8-Br-cAMP, 8-Br-cGMP, and VUAA1 (n=4). Holding potentials for all recordings were −60 mV. (FIG. 8C) Representative trace from cells expressing rCNGA2 with application of 8-Br-cGMP. Holding potentials for all recording were −60 mV. (FIG. 8D) Histogram of normalized currents from cyclic nucleotide and control responses (n=5).

DETAILED DESCRIPTION OF THE PREFERRED EMBODIMENTS

Figure 1:
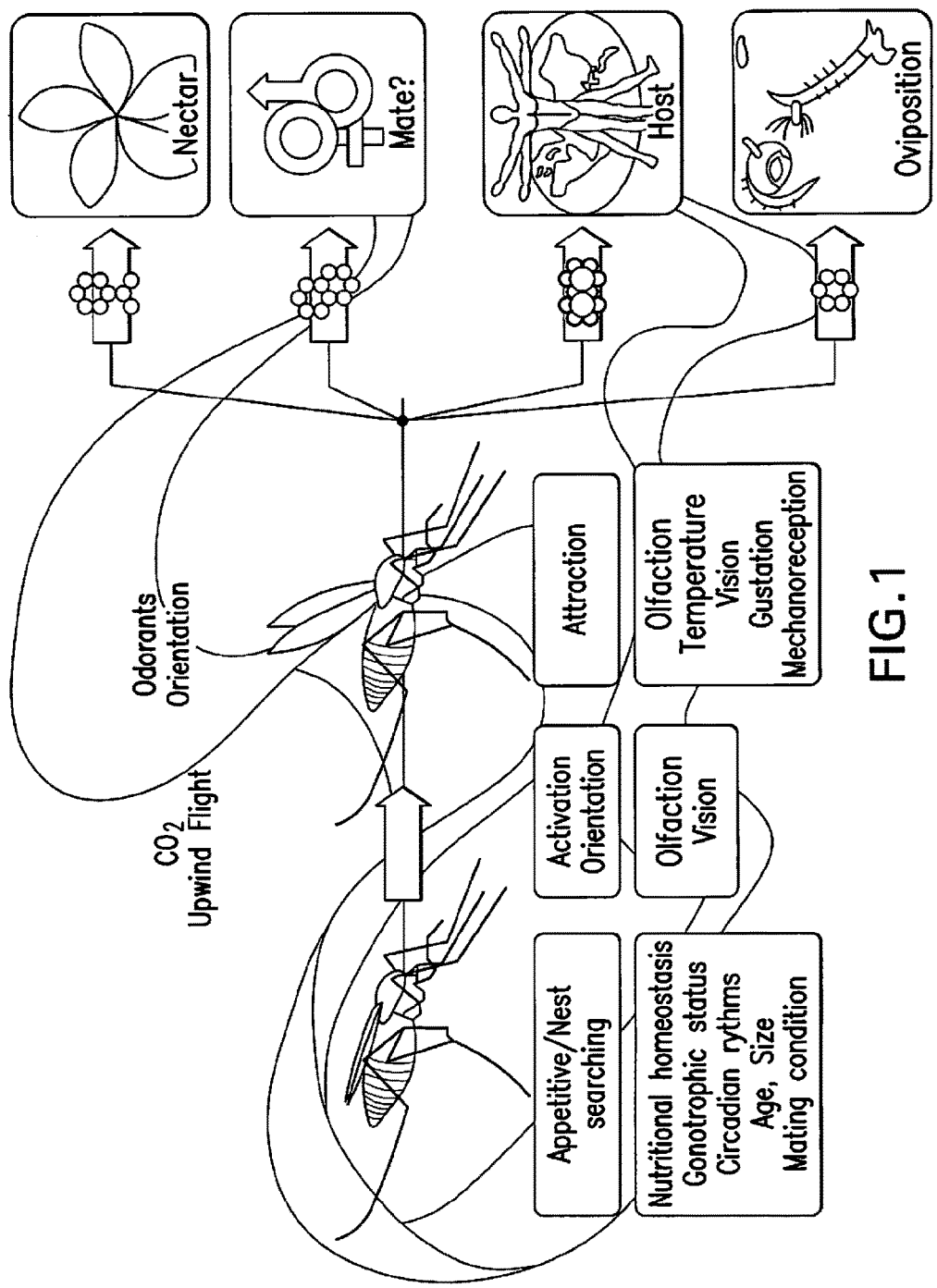
FIG. 1. Olfactory cues make up the principal sensory modalities in mediating several key behaviors in adult mosquitoes. These include nectar feeding, selection of oviposition sites, mate selection and especially host (blood-meal) preference where chemical and temperature inputs synergize most.

Insects interpret their chemical environment through the use of a family of cell-surface odorant receptors (ORs) to sense volatile chemicals known as odorants. For odorant reception to take place, a member of the ORco family of ORs must be present to couple to another highly diverse OR (ORX) that is responsible for sensing different odors. Each insect species has many Ors that generally species-specific, but only one Orco family member that are extremely conserved throughout all insect taxa. There have been no reported ORco ligands to date. As part of a High-Throughput Screen to identify compounds that modulate OR activity, the present inventors have discovered the first ORco family activator. This ORco family activator, termed VUAA1, has the theoretical ability to activate all ORX/ORco complexes. The host-seeking behavior of blood-feeding insects is principally driven through their sense of smell. This blood-feeding behavior serves as the foundation for their ability to transit disease. The capacity to disrupt olfactory-mediated behavior through direct chemical interference, as by VUAA1, would be a major advance in the fight against vector-borne diseases, and modulation of the ORco complex would render the insect incapable of performing its usual behaviors, such as host-seeking and nectar feeding. VUAA1 can also be used to disrupt the behavior of agriculturally important insect pests responsible for billions of dollars of crop damage worldwide each year.

I. MOSQUITOES

Mosquito, from the Spanish or Portuguese meaning "little fly," is a common insect in the family Culicidae. Mosquitoes resemble crane flies (family Tipulidae) and chironomid flies (family Chironomidae), with which they are sometimes confused by the casual observer.

Mosquitoes go through four stages in their life-cycle: egg, larva, pupa, and adult or imago. Adult females lay their eggs in water, which can be a salt-marsh, a lake, a puddle, a natural reservoir on a plant, or an artificial water container such as a plastic bucket. The first three stages are aquatic and last 5-14 days, depending on the species and the ambient temperature; eggs hatch to become larvae, then pupae. The adult mosquito emerges from the pupa as it floats at the water surface. Adults live for 4-8 weeks.

Female mosquitoes have mouthparts that are adapted for piercing the skin of plants and animals. While males typically feed on nectar and plant juices, the female needs to obtain nutrients from a "blood meal" before she can produce eggs.

Mosquito larvae have a well-developed head with mouth brushes used for feeding, a large thorax with no legs and a segmented abdomen. Larvae breathe through spiracles located on the eighth abdominal segment, or through a siphon, and therefore must come to the surface frequently. The larvae spend most of their time feeding on algae, bacteria, and other micro-organisms in the surface microlayer. They dive below the surface only when disturbed. Larvae swim either through propulsion with the mouth brushes, or by jerky movements of the entire body. Larvae develop through four stages, or instars, after which they metamorphose into pupae. At the end of each instar, the larvae molt, shedding their exoskeleton, or skin, to allow for further growth. Length of the adult varies but is rarely greater than 16 mm (0.6 in), and weight up to 2.5 mg (0.04 grain). All mosquitoes have slender bodies with three sections: head, thorax and abdomen.

The pupa is comma-shaped, as in *Anopheles* when viewed from the side. The head and thorax are merged into a cephalothorax with the abdomen circling around underneath. As with the larvae, pupae must come to the surface frequently to breathe, which they do through a pair of respiratory trumpets on the cephalothorax. However, pupae do not feed during this stage. After a few days, the dorsal surface of the cephalothorax splits and the adult mosquito emerges. The pupa is less active than larva.

The duration from egg to adult varies among species and is strongly influenced by ambient temperature. Mosquitoes can develop from egg to adult in as little as five days but usually take 10-14 days in tropical conditions. The variation of the body size in adult mosquitoes depends on the density of the larval population and food supply within the breeding water. Adult flying mosquitoes frequently rest in a tunnel that they build right below the roots of the grass.

Adult mosquitoes usually mate within a few days after emerging from the pupal stage. In most species, the males form large swarms, usually around dusk, and the females fly into the swarms to mate.

Males live for about a week, feeding on nectar and other sources of sugar. Females will also feed on sugar sources for energy but usually require a blood meal for the development of eggs. After obtaining a full blood meal, the female will rest for a few days while the blood is digested and eggs are developed. This process depends on the temperature but usually takes 2-3 days in tropical conditions. Once the eggs are fully developed, the female lays them and resumes host seeking. The cycle repeats itself until the female dies. Their lifespan depends on temperature, humidity, and also their ability to successfully obtain a blood meal while avoiding host defenses.

The head is specialized for acquiring sensory information and for feeding. The head contains the eyes and a pair of long, many-segmented antennae. The antennae are important for detecting host odors as well as odors of breeding sites where females lay eggs. In all mosquito species, the antennae of the males in comparison to the females are noticeably bushier and contain auditory receptors to detect the characteristic whine of the female. The compound eyes are distinctly separated from one another. Their larvae only possess a pit-eye ocellus. The compound eyes of adults develop in a separate region of the head. New ommatidia are added in semicircular rows at the rear of the eye; during the first phase of growth, this leads to individual ommatidia being square, but later in development they become hexagonal. The hexagonal pattern will only become visible when the carapace of the stage with square eyes is molted. The head also has an elongated, forward-projecting "stinger-like" proboscis used for feeding, and two sensory palps. The maxillary palps of the males are longer than their proboscis whereas the females' maxillary palps are much shorter. As with many members of the mosquito family, the female is equipped with an elongated proboscis that she uses to collect blood to feed her eggs.

The thorax is specialized for locomotion. Three pairs of legs and a pair of wings are attached to the thorax. The insect wing is an outgrowth of the exoskeleton. The *Anopheles* mosquito can fly for up to four hours continuously at 1 to 2 kilometers per hour (0.62 to 1.2 mph) travelling up to 12 km (7.5 mi) in a night.

The abdomen is specialized for food digestion and egg development. This segmented body part expands considerably when a female takes a blood meal. The blood is digested over time serving as a source of protein for the production of eggs, which gradually fill the abdomen.

The duration from egg to adult varies among species and is strongly influenced by ambient temperature. Mosquitoes can develop from egg to adult in as little as five days but usually take 10-14 days in tropical conditions. The variation of the body size in adult mosquitoes depends on the density of the larval population and food supply within the breeding water. Adult flying mosquitoes frequently rest in a tunnel that they build right below the roots of the grass.

Adult mosquitoes usually mate within a few days after emerging from the pupal stage. In most species, the males form large swarms, usually around dusk, and the females fly into the swarms to mate. Males live for about a week, feeding on nectar and other sources of sugar. Females will also feed on sugar sources for energy but usually require a blood meal for the development of eggs. After obtaining a full blood meal, the female will rest for a few days while the blood is digested and eggs are developed. This process depends on the temperature but usually takes 2-3 days in tropical conditions. Once the eggs are fully developed, the female lays them and resumes host seeking. The cycle repeats itself until the female dies. Their lifespan depends on temperature, humidity, and also their ability to successfully obtain a blood meal while avoiding host defenses.

In order for the mosquito to obtain a blood meal it must circumvent the vertebrate physiological responses. The mosquito, as with all blood-feeding arthropods, has mechanisms to effectively block the hemostasis system with their saliva, which contains a mixture of secreted proteins. Mosquito saliva negatively affects vascular constriction, blood clotting, platelet aggregation, angiogenesis and immunity and creates inflammation. Universally, hematophagous arthropod saliva contains at least one anticlotting, one antiplatelet, and one vasodilatory substance. Mosquito saliva also contains enzymes that aid in sugar feeding and antimicrobial agents to control bacterial growth in the sugar meal. The composition of mosquito saliva is relatively simple as it usually contains fewer than 20 dominant proteins. Despite the great strides in knowledge of these molecules and their role in bloodfeeding achieved recently, scientists still cannot ascribe functions to more than half of the molecules found in arthropod saliva. One promising application is the development of anti-clotting drugs based on saliva molecules, which might be useful for approaching heart-related disease, because they are more user-friendly blood clotting inhibitors and capillary dilators.

Two important events in the life of female mosquitoes are egg development and blood digestion. After taking a blood meal the midgut of the female synthesizes proteolytic enzymes that hydrolyze the blood proteins into free amino acids. These are used as building blocks for the synthesis of egg yolk proteins.

II. MOSQUITO-BORNE DISEASE

Mosquitoes are a vector agent that carries disease-causing viruses and parasites from person to person without catching the disease themselves. The principal mosquito borne diseases are the viral diseases yellow fever, dengue fever and Chikungunya, transmitted mostly by the *Aedes aegypti*, and malaria carried by the genus *Anopheles*. Though originally a public health concern, HIV is now thought to be almost impossible for mosquitoes to transmit.

Mosquitoes are estimated to transmit disease to more than 700 million people annually in Africa, South America, Central America, Mexico and much of Asia with millions of resulting deaths. At least 2 million people annually die of these diseases.

Methods used to prevent the spread of disease, or to protect individuals in areas where disease is endemic include vector control aimed at mosquito eradication, disease prevention, using prophylactic drugs and developing vaccines and prevention of mosquito bites, with insecticides, nets and repellents. Since most such diseases are carried by "elderly" females, scientists have suggested focusing on these to avoid the evolution of resistance.

A. Protozoa

The mosquito genus *Anopheles* carries the malaria parasite (see *Plasmodium*). Worldwide, malaria is a leading cause of premature mortality, particularly in children under the age of five. It is widespread in tropical and subtropical regions, including parts of the Americas (22 countries), Asia, and Africa. Each year, there are approximately 350-500 million cases of malaria, killing between one and three million people, the majority of whom are young children in sub-Saharan Africa. Ninety percent of malaria-related deaths occur in sub-Saharan Africa. Malaria is commonly associated with poverty, and can indeed be a cause of poverty and a major hindrance to economic development.

Five species of the *plasmodium* parasite can infect humans; the most serious forms of the disease are caused by

*Plasmodium falciparum.* Malaria caused by *Plasmodium vivax, Plasmodium ovale* and *Plasmodium malariae* causes milder disease in humans that is not generally fatal. A fifth species, *Plasmodium knowlesi*, is a zoonosis that causes malaria in macaques but can also infect humans.

Malaria is naturally transmitted by the bite of a female *Anopheles* mosquito. When a mosquito bites an infected person, a small amount of blood is taken, which contains malaria parasites. These develop within the mosquito, and about one week later, when the mosquito takes its next blood meal, the parasites are injected with the mosquito's saliva into the person being bitten. After a period of between two weeks and several months (occasionally years) spent in the liver, the malaria parasites start to multiply within red blood cells, causing symptoms that include fever, and headache. In severe cases the disease worsens leading to hallucinations, coma, and death.

A wide variety of antimalarial drugs are available to treat malaria. In the last 5 years, treatment of *P. falciparum* infections in endemic countries has been transformed by the use of combinations of drugs containing an artemisinin derivative. Severe malaria is treated with intravenous or intramuscular quinine or, increasingly, the artemisinin derivative artesunate. Several drugs are also available to prevent malaria in travellers to malaria-endemic countries (prophylaxis). Resistance has developed to several antimalarial drugs, most notably chloroquine.

Malaria transmission can be reduced by preventing mosquito bites by distribution of inexpensive mosquito nets and insect repellents, or by mosquito-control measures such as spraying insecticides inside houses and draining standing water where mosquitoes lay their eggs. Although many are under development, the challenge of producing a widely available vaccine that provides a high level of protection for a sustained period is still to be met.

B. Helminthiasis

Some species of mosquito can carry the filariasis worm, a parasite that causes a disfiguring condition (often referred to as elephantiasis) characterized by a great swelling of several parts of the body; worldwide, around 40 million people are living with a filariasis disability. The thread-like filarial nematodes (roundworms) are members of the superfamily Filarioidea, also known as "filariae." There are 9 known filarial nematodes which use humans as the definitive host. These are divided into 3 groups according to the niche within the body that they occupy: lymphatic filariasis, subcutaneous filariasis, and serous cavity filariasis. Lymphatic filariasis is caused by the worms *Wuchereria bancrofti, Brugia malayi,* and *Brugia timori*. These worms occupy the lymphatic system, including the lymph nodes, and in chronic cases these worms lead to the disease elephantiasis. Subcutaneous filariasis is caused by *loa loa* (the African eye worm), *Mansonella streptocerca, Onchocerca volvulus,* and *Dracunculus medinensis* (the guinea worm). These worms occupy the subcutaneous layer of the skin, in the fat layer. Serous cavity filariasis is caused by the worms *Mansonella perstans* and *Mansonella ozzardi*, which occupy the serous cavity of the abdomen. In all cases, the transmitting vectors are either blood sucking insects (flies or mosquitoes), or copepod crustaceans in the case of *Dracunculus medinensis.*

Individuals infected by filarial worms may be described as either "microfilaraemic" or "amicrofilaraemic," depending on whether or not microfilaria can be found in their peripheral blood. Filariasis is diagnosed in microfilaraemic cases primarily through direct observation of microfilaria in the peripheral blood. Occult filariasis is diagnosed in amicrofilaraemic cases based on clinical observations and, in some cases, by finding a circulating antigen in the blood.

C. Viruses

The viral disease yellow fever, an acute hemorrhagic disease, is transmitted mostly by *Aedes aegypti* mosquitoes. The virus is a 40 to 50 nm enveloped RNA virus with positive sense of the Flaviviridae family. The yellow fever virus is transmitted by the bite of female mosquitoes (the yellow fever mosquito, *Aedes aegypti*, and other species) and is found in tropical and subtropical areas in South America and Africa, but not in Asia. The only known hosts of the virus are primates and several species of mosquito. The origin of the disease is most likely to be Africa, from where it was introduced to South America through the slave trade in the 16th century. Since the 17th century, several major epidemics of the disease have been recorded in the Americas, Africa and Europe. In the 19th century, yellow fever was deemed one of the most dangerous infectious diseases.

Clinically, yellow fever presents in most cases with fever, nausea, and pain and it generally subsides after several days. In some patients, a toxic phase follows, in which liver damage with jaundice (giving the name of the disease) can occur and lead to death. Because of the increased bleeding tendency (bleeding diathesis), yellow fever belongs to the group of hemorrhagic fevers. The WHO estimates that yellow fever causes 200,000 illnesses and 30,000 deaths every year in unvaccinated populations; around 90% of the infections occur in Africa.

A safe and effective vaccine against yellow fever has existed since the middle of the 20th century and some countries require vaccinations for travelers. Since no therapy is known, vaccination programs are, along with measures to reduce the population of the transmitting mosquito, of great importance in affected areas. Since the 1980s, the number of cases of yellow fever has been increasing, making it a reemerging disease.

Dengue fever and dengue hemorrhagic fever (DHF) are acute febrile diseases also transmitted by *Aedes aegypti* mosquitoes. These occur in the tropics, can be life-threatening, and are caused by four closely related virus serotypes of the genus *Flavivirus*, family Flaviviridae. It is also known as breakbone fever, since it can be extremely painful. It occurs widely in the tropics, and increasingly in southern China. Unlike malaria, dengue is just as prevalent in the urban districts of its range as in rural areas. Each serotype is sufficiently different that there is no cross-protection and epidemics caused by multiple serotypes (hyperendemicity) can occur. Dengue is transmitted to humans by the *Aedes (Stegomyia) aegypti* or more rarely the *Aedes albopictus* mosquito. The mosquitoes that spread dengue usually bite at dusk and dawn but may bite at any time during the day, especially indoors, in shady areas, or when the weather is cloudy. The WHO says some 2.5 billion people, two fifths of the world's population, are now at risk from dengue and estimates that there may be 50 million cases of dengue infection worldwide every year. The disease is now endemic in more than 100 countries.

Other viral diseases like epidemic polyarthritis, Rift Valley fever, Ross River Fever, St. Louis encephalitis, West Nile virus (WNV), Japanese encephalitis, La Crosse encephalitis and several other encephalitis type diseases are carried by several different mosquitoes. Eastern equine encephalitis (EEE) and Western equine encephalitis (WEE) occurs in the United States where it causes disease in humans, horses, and some bird species. Because of the high mortality rate, EEE and WEE are regarded as two of the most serious mosquito-borne diseases in the United States. Symptoms range from mild flu-like illness to encephalitis, coma and death. *Culex* and *Culiseta* are also involved in the transmission of disease. WNV has recently been a concern in the United States, prompting aggressive mosquito control programs.

D. Transmission

A mosquito's period of feeding is often undetected; the bite only becomes apparent because of the immune reaction it provokes. When a mosquito bites a human, she injects saliva and anti-coagulants. For any given individual, with the initial bite there is no reaction but with subsequent bites the body's immune system develops antibodies and a bite becomes inflamed and itchy within 24 hours. This is the usual reaction in young children. With more bites, the sensitivity of the human immune system increases, and an itchy red hive appears in minutes where the immune response has broken capillary blood vessels and fluid has collected under the skin. This type of reaction is common in older children and adults. Some adults can become desensitized to mosquitoes and have little or no reaction to their bites, while others can become hyper-sensitive with bites causing blistering, bruising, and large inflammatory reactions, a response known as Skeeter Syndrome.

III. INSECT OLFACTORY RECEPTORS

The ability to detect and respond to the chemical environment is critical sensory input into many essential behaviors of hematophagous (blood-feeding) insects (Zwiebel and Takken, 2004; FIG. 1). The search for vertebrate blood meals typically involves a flight of some distance to reach the host. This behavior consists of a series of behavioral stages, beginning with the activation of a receptive insect by the host chemical odor (kairomone) and ending when the insect alights on the host (Takken, 1991). At close range, attraction is mediated by several odorants, one of which is $CO_2$. In combination with other host-derived organic chemicals, $CO_2$ acts as a synergist as it greatly enhances the attraction triggered by other volatiles (Gilles, 1980). Moreover, it appears that mosquitoes respond to changes in the concentration of CO2, rather than its presence or absence. In *Ae. aegypti*, changes in the firing rate of $CO_2$ receptors have been observed with increases in concentration of as little as 0.01% (Kellogg, 1970), while alterations in behavior have been observed after increases of 0.03-0.05% (Eiras and Jepson, 1991). Furthermore, a close examination of the role of $CO_2$ revealed that the turbulence of the odor plume in the laboratory greatly affected the responsiveness of *Ae. aegypti* and *An. gambiae* s.s. (Dekker et al., 2001a).

*An. gambiae* has also been shown to be attracted to acetone, lactic acid (Acree et al., 1968), carboxylic acids (Meijerink and van Loon, 1999), ammonia, 4-methyl-phenol, 1-octen-3-ol and other components of sweat (Cork and Park, 1996; Meijerink et al., 2001), as well as to the odor of human feet, expired air and several unidentified components of Limburger cheese (De Jong and Knols, 1995). Furthermore, the often-cited differences in human attractiveness for mosquitoes (Curtis, 1986) is almost certainly olfactory based (Qiu et al., 2006a; Schreck et al., 1990). This within-host differential behavior is most particularly expressed in anthropophilic culicids such as *Ae. aegypti* and *An. gambiae* s.s. (de Jong and Knols, 1995; Lindsay et al., 1993; Schreck et al., 1990). Host age but not gender may affect these inter-individual differences (Carnevale et al., 1978); race also appears to have no effect (Schreck et al., 1990). Young children have been shown to be less attractive to Anophelines than adults (Muirhead-Thomson, 1951; Thomas, 1951). Studies on the chemical composition of human volatiles (Bernier et al., 1999; Krotoszynski et al., 1977; Labows, 1979) revealed the existence of a large number (>350) of chemicals, and work is in progress to study the most important components of these volatiles regulating mosquito behavior. Lastly, it is also clear that responses to $CO_2$ affect inter-individual differences in attractiveness (Brady et al., 1997) and, thus, $CO_2$ serves as a universal attractant to many mosquito species (Gillies, 1980; Takken et al., 1997; Takken and Knols, 1999). It has been reported that $CO_2$ stimulation synergizes with host body odor and has an activating effect on host-seeking anopheline mosquitoes, inducing take-off and sustained flight behaviors (Dekker et al., 2001b; Gillies, 1980; Mboera and Takken, 1997).

Figure 2:
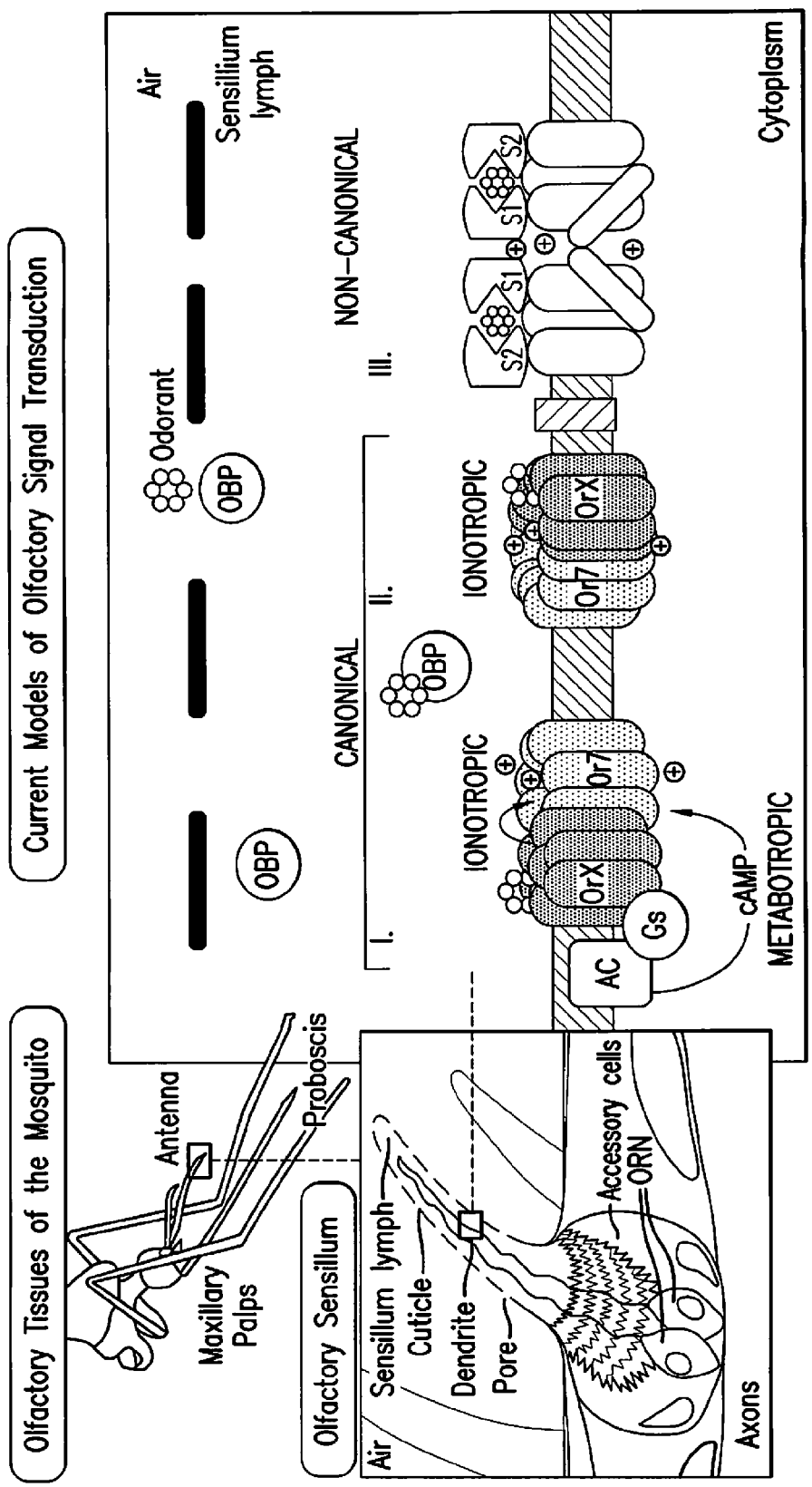
FIG. 2. Canonical and Non-Canonical Models of General Insect Olfactory Signal Transduction. Schematic incorporating recent insights into molecular interactions in the lumen and dendritic membrane of insect ORNs. General odorants entering through cuticular pores are loaded onto OBPs that facilitate transport to conventional ORs (ORx) within the context of canonical OR complexes. Transport of odorants is directed by a specific OBP which may physically interact with the conventional and/or Orco family OR. Pheromone-sensitive pathways are likely to involve additional molecular components. In canonical models (I, II), conventional ORs (OrX) bind odorants and physically interact with highly conserved, non-conventional Orco family ORs (AgO7 in *An. gambiae*) to form functional heteromultimers expressed in a majority of ORNs. In this model, binding of odorants activate ionotropic (Sato et al., 2008) and, possibly, metabotropic (Wicher et al., 2008) signaling pathways. In other ORNs, non-canonical ORs (III), such as members of the IGluR/IR gene family (Benton et al., 2009) respond to atypical odorant that in some cases (e.g., ammonia and lactic acid) are associated with human-derived kairomones.

In a process that is analogous to the sense of smell in humans as well as other insects, mosquito olfactionis initiated by the process of chemosensory signal transduction by which chemical signals (typically environmental cues) are translated into neuronal activity and, ultimately, behavioral outputs. In *An. gambiae*, this takes place within specialized hair-like structures called sensilla that are dispersed throughout the antennae and other head appendages on adult and larval-stage anopheline mosquitoes (Zwiebel and Takken, 2004; FIG. 2).

Until recently, much of the inventors' view of insect olfactory signal transduction at the molecular level has been strongly influenced by observations made in vertebrates, crustaceans and nematodes (Hildebrand and Shepherd, 1997; Krieger and Breer, 1999). The canonical model involves a family of heptahelical G-protein-coupled receptors (GPCRs) that activate downstream effectors via heterotrimeric GTP-binding (G) proteins and traditional second messengers. It has long been assumed, although not fully accepted (see below), that the canonical model of olfactory signal transduction would also hold true in insects, in which several of the "usual" molecular suspects have been identified and, in part, functionally characterized. These include arrestins (Merrill et al., 2002; 2003; 2005), odorant-binding proteins (OBPs) (Pelosi and Maida, 1995), a heterotrimeric G-protein (Laue et al., 1997) as well as a CNG (Baumann et al., 1994; Krieger et al., 1999) and an IP3-gated ion channel (Stengl, 1994). In one study using the cockroach, it was demonstrated that pheromone exposure of insect antennal preparations caused a rapid increase in IP3 levels (Breer et al., 1990), which in a follow-up study could be inhibited by pertussis toxin (Boekhoff et al., 1990), indicating that the IP3 increase is dependent on either a Gαi or a Gαo G-protein subunit. More recently, the inventors carried out a molecular survey of G-protein expression in the olfactory appendages of *An. gambiae*, in which Gαq localization consistent with involvement in olfactory signal transduction was observed along the dendrites of most olfactory sensory neurons (Rutzler et al., 2006). Furthermore, pheromone receptor neuron activity of *Bombyx mori* could be stimulated with fluoride ions (Laue et al., 1997), which are known to activate heterotrimeric G proteins via binding to the a subunit in combination with magnesium ions (Antonny et al., 1993). However, despite this growing wealth of information, the precise mode of insect olfactory signal transduction remains largely obscure and is therefore the subject of ongoing investigation that has raised serious issues with regard to the validity of GPCR-based paradigms.

Because olfaction was mediated by GPCRs in both vertebrates and at least one invertebrate, it was assumed that insects would also utilize these proteins in olfactory signal transduction. Indeed, using a variety of approaches, a large family of candidate ORs has been identified in *D. melano-*

*gaster* (Clyne et al., 1999) (Gao and Chess, 1999; Vosshall et al., 1999). In the first of these studies, putative *D. melanogaster* Ors (*Dors*) were identified using a novel computer algorithm that searched for conserved physicochemical features common to known transmembrane proteins (Kim et al., 2000) rather than relying on a sequence homology-based screen (which might miss a divergent member of a particular family). The structures that were ultimately identified using these strategies led to the identification of a highly divergent family of receptors, displaying between 10% and 75% identity and bearing no significant homology to any other GPCR family (Smith, 1999). Another chemosensory receptor family was also described in *D. melanogaster* and *An. gambiae* and is presumed to comprise gustatory (taste) receptors (Clyne et al., 2000; Hill et al., 2002; Scott et al., 2001). The other circumstantial criterion to infer olfactory function has been provided by various in situ expression pattern studies that have demonstrated that the majority of these genes were selectively and stereotypically expressed in the fly olfactory sensory neurons (Clyne et al., 1999) (Elmore and Smith, 2001; Gao and Chess, 1999; Vosshall, 2001; Vosshall et al., 1999). Two-color (double-labeling) in situ hybridization suggests that, with two notable caveats (Goldman et al., 2005), most *D. melanogaster* ORNs are likely to express a single DOR gene (Vosshall et al., 2000), which is analogous to mammalian systems (Mombaerts, 1999), but in stark contrast to the *C. elegans* system. One apparent exception to the one ORN-one receptor principle is the non-conventional DOR83b, now known as DmORco. Unlike most other DORs, DmORco is expressed throughout the majority of antennal and maxillary palp ORNs of *D. melanogaster*. Putative DmORco orthologs have been identified in a wide range of insect species and share many characteristics, including high sequence identity (Pitts et al., 2004), characteristic broad expression pattern (Krieger et al., 2003) and conserved functions (Jones et al., 2005). ORco family members are considered non-conventional ORs as they act as general dimerization partners for other members of the DOR family (Larsson et al., 2004). More recently, Benton, Vosshall and co-workers have identified a novel set of ionotropic glutamate receptors as a new class of insect chemosensory receptors (IRs) that are expressed in DmOrco-ORNs associated with coeloconic sensilla where they act in parallel with "classical" insect ORs to respond to ammonia and other environmental cues (Benton et al., 2009; Liu et al., 2010).

Elegant studies by the Vosshall lab have also suggested that insect ORs manifest a novel topology relative to vertebrate ORs (Benton et al., 2006). In the absence of actual structural information insect ORs have been structurally characterized largely based on bioinformatic models derived from vertebrates (Clyne et al., 2000; Vosshall et al., 1999). Indeed, while sequence-based phylogenies recognize that insect ORs in general comprise a distinct family of hepta-helical receptors that are an expanded lineage of ancestral chemosensory receptors (Mombaerts, 1999; Robertson et al., 2003) there is a growing awareness that insect ORs are likely to represent a structurally unique set of sensory proteins. These studies provide compelling evidence in support of the view that *Drosophila* ORs are heteromeric complexes between the non-conventional DmORco and conventional, odorant binding DORs that adopt a novel membrane topology in which the N-terminus is intracellular rather than the extra-cellular localization that is typical of vertebrate ORs and GPCRs (Benton et al., 2006). Independent validation (Lundin et al., 2007) together with recent computational analyses employing hidden Markov modeling that "strongly rejects" classifying arthropod ORs as GPCRs (Wistrand et al., 2006) raise significant concerns regarding the nature of the signaling pathways that are downstream of odorant activation in insects. Indeed, two recent studies provide provocative evidence to suggest that *Drosophila* ORs manifest properties of both ligand-gated (Sato et al., 2008) and cyclic-nucleotide-gated ion channels (Wicher et al., 2008). While these hypotheses still differ in their particulars, there is growing awareness that insect olfactory transduction may diverge from vertebrate paradigms and act as non-GPCR-mediated ion-channels (FIG. 2). In any case, while current hypotheses may differ, the growing possibility that insect olfactory transduction may diverge from vertebrate paradigms and act via non-GPCR-mediated mechanisms such as ion channels (FIG. 2) are compelling.

In the first report of insect ORs outside of the model insect system *D. melanogaster*, members of the inventors' laboratory, as part of a collaborative effort with Drs. John Carlson and Hugh Robertson, were responsible for the identification of a set of candidate Or genes selectively expressed in olfactory tissues of *An. gambiae* (AgORs) (Fox et al., 2001). Moreover, that report also demonstrated that at least one of the initial set of AgORs displays female-specific expression, a feature that may be especially relevant for disease transmission. In a subsequent study, as part of the effort to annotate the recently completed genomic sequence of *An. gambiae* (Holt et al., 2002), the inventors (in collaboration with other groups) utilized bioinformatics and molecular approaches to describe the entire *An. gambiae* GPCR gene family (AgGPCRs); of the 275 putative AgG-PCRs, 79 candidate AgORs were described (Hill et al., 2002). Furthermore, a similar bioinformatic approach (using a non-public database) has been used to identify nine candidate Or genes in the heliothine moth *Heliothis virescens* (Krieger et al., 2002), some of which share sequence homology with AgOrs. More recently, a large family of candidate Or genes have been identified in the genome sequence of the honey bee, *Apis mellifera* (Robertson and Wanner, 2006), *Ae. aegypti* (Bohbot et al., 2007) and the red flour beetle, *Tribolium casteneum* (Engsontia et al., 2008).

Thus far, insect ORs have been extensively deorphanized in a number of heterologous systems. The first successful functional studies of insect ORs were carried out for DOR43a using a *Xenopus* oocyte expression system (Wetzel et al., 2001), and over-expression in *D. melanogaster* (Storkuhl and Kettler, 2001) showed increased sensitivity to a set of four odorants. The Carlson laboratory has used a novel experimental approach that takes advantage of a genetic strain of *D. melanogaster* in which a chromosomal deletion has resulted in the loss of the endogenous receptors (DOR22a/b) from the ab3A ORN. The resultant formation of a the "empty neuron" system facilitates the specific targeting of exogenous OR genes into the empty neuron, thereby allowing electrophysiological assessment of the ability of the novel receptor to carry out chemosensory signal transduction within the ab3A neuron upon stimulation with a diverse set of odorants (Dobritsa et al., 2003). This system has been used effectively to functionally characterize nearly all the DORs (Hallem et al., 2004a) (Hallem and Carlson, 2006), leading to a highly developed map of the multidimensional "odor space" of the DORs. As part of a long-standing collaboration between the Carlson lab and that of the inventors, multiple AgOR have also been functionally characterized in the *Drosophila* empty neuron (Hallem et al., 2004b; Lu et al., 2007). These studies, along with the success in functionally expressing over 40 AgORs in *Xeno-* pus and cell culture systems have lead to significant advances in understanding the molecular basis for olfactory sensitivity in larval (Xia et al., 2008) and adult (Lu et al., 2007) *An. gambiae*. For example, $CO_2$ which acts as universal attractant for many species of mosquitoes (Takken and Knols, 1999) elicits avoidance in *Drosophila* where it has been identified as an active component of the "stress odorant" that targets a discrete population of sensory neurons (Suh et al., 2007) and where a pair of highly conserved putative gustatory receptors (Gr21a and Gr63a) have been shown to both be both necessary and sufficient to mediate olfactory sensitivity to CO2 in *Drosophila* (Jones et al., 2007; Kwon et al., 2007). As part of a comprehensive study of the olfactory processes on the maxillary palp in *An gambiae*, the inventors have identified three Gr21a/63a homologs (AgGrs22-24) as the molecular partners required that together comprise the anopheline $CO_2$ receptor (Lu et al., 2007).

IV. ACTIVE AGENTS

In accordance with the present invention, there is provided an agent shown below and designated throughout as VUAA1:

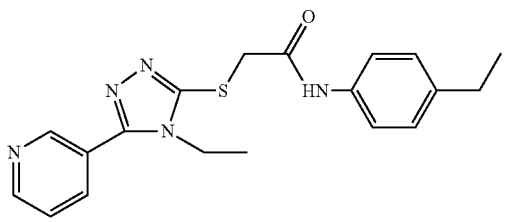 [SMILES: CCc1ccc(NC(=O)CSc2nnc(-c3cccnc3)n2CC)cc1]

This compound was identified through the screening procedure described in the Examples.

It is also contemplated that that the concentrations of the active agent can vary. In non-limiting embodiments, for example, the compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein. In non-limiting aspects, the percentage can be calculated by weight or volume of the total composition. A person of ordinary skill in the art would understand that the concentrations can vary depending on the addition, substitution, and/or subtraction of the compounds, agents, or active ingredients, to the disclosed methods and compositions.

V. FORMULATIONS FOR ACTIVE AGENTS

In one embodiment, the present agent provides topical formulations including agents of the present invention. Including the active agent, such formulations will contain a variety of compounds and compositions that are typical for use with topical delivery. The following is a discussion of agents for use in preparation of topical formulations.

A. Film Forming Agents

Film formers are materials or compound, which, upon drying, can produce a continuous film on skin. This can increase the durability of a composition while also resulting in reduced moisture loss from skin. The CTFA Handbook at volume 3, pages 3187-3192, provides a wide range of film formers that can be used in the context of the present invention, all of which are incorporated by reference. Non-limiting examples of such film formers include Polysilicone-6, Polysilicone-8, Polysilicone-11, Polysilicone-14, VP/Dimethiconylacrylate/Polycarbamyl/Polyglycol Ester, VP/Dimethylaminoethylmethacrylate Copolymer, VP/Dimethylaminoethylmethacrylate/Polycarbamyl Polyglycol Ester, VP/Eicosene Copolymer, VP/Hexadecene Copolymer, VP/Methacrylamide/Vinyl Imidazole Copolymer, VP/Polycarbamyl Polyglycol Ester, VP/VA Copolymer, Polyester-1, Polyester-2, Polyester-3, Polyester-4, Polyester-5, Polyester-7, Polyester-8, and Polyester-10.

B. Ester Containing Solvents

Esters are covalent compounds formed between acids and alcohols. They can be used to stabilize and solubilize agents in the context of the present invention. The CTFA Handbook at volume 3, pages 3079-3088, provides a wide range of ester containing solvents that can be used in the context of the present invention, all of which are incorporated by reference. Non-limiting examples of such solvents include C12-15 Alkyl benzoate, neopentyl glycol diheptanoate, dipropylene glycol dibenzoate, and PPG-15 stearyl ether benzoate.

C. Gelling Agents

The composition of the present invention can be formulated as a transparent gel. Gelling agents such as dimethicone/bis-isobutyl PPG-20 crosspolymer can used to create the gel-based primer. Further, a wide range of gelling agents are commercially available from Dow Corning (Midland, Mich. (USA)). A non-limiting example includes Dow Corning EL-8050 ID, which is a blend of dimethicone/bisisobutyl PPG-20 crosspolymer and isododecane.

D. Additional Skin Conditioning Agents and Emollients

Non-limiting examples of skin conditioning agents and emollients that can be used with the compositions of the present invention include amino acids, chondroitin sulfate, diglycerin, erythritol, fructose, glucose, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea *officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, tructose, gelatin, geranium *maculatum* oil, glucosamine, glucose glutamate, glutamic acid, glycereth-26, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica* limonum) oil, linoleic acid, linolenic acid, macadamia *ternifolia* nut oil, magnesium stearate, magnesium sulfate, maltitol, *matricaria* (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopheryl linoleate, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

E. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl linoleate, tocopheryl nicotinate, tocopheryl succinate, and tris(nonylphenyl)phosphite.

F. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

G. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

H. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O-chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e., dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

I. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

J. Thickening Agents

Thickening agents include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; and 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboyxmethyl dextran, sodium carrageenan, tragacanth gum, xanthan gum, and mixtures thereof.

K. Vehicles

The compositions of the present invention can be incorporated into all types of are effective in all types of vehicles. Non-limiting examples of suitable vehicles include emulsions (e.g., water-in-oil, water-in-oil-in-water, oil-in-water, -oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and active agents be selected in such a way that the combinations are chemically compatible and do not form complexes which precipitate from the finished product.

VI. ARTICLES OF MANUFACTURE

The present invention contemplates the use of the VUAA1 agent in the manufacture of certain items. The material may be pre-made and then dipped, painted or sprayed with the agent. Alternatively, the materials may be formed in the presence of the agent so as to incorporate the agent integrally thereinto.

For example, VUAA1 may be used to coat or impregnate various articles of manufacture, the use of which can help deliver VUAA1 to a mosquito environment and/or protect a user of the article from mosquito contact. Such articles include netting, such as the type use to exclude insects from dwelling (i.e., in windows and door ways) or to exclude insects from a particular location, such as a bed or room.

Other articles of manufacture include clothing or fabric from which clothing can be produced. Clothing includes hats, veils, masks, shoes and gloves, as well as shirts, pants and underwear. Other articles include bedding, such as sheets, blankets, pillow cases, and mattresses. Still additional articles include tarps, tents, awnings, door flaps, screens, or drapes.

VII. AGENT DELIVERY SYSTEMS

A. Misting Systems

The active agent of the present invention may, in one embodiment, be advantageously dispersed into an environment using a misting system. The environment may be a single family dwelling yard, and street, a neighborhood, a subdivision, a township or a city. Examples of misting systems are shown in U.S. Pat. Nos. 7,306,167 and 7,090,147, and U.S. Patent Publication 2006/0260183, both of which are hereby incorporated by reference.

B. Baits and Pellets

In many cases, it would be desirable to apply the agent of the present invention in solid form. Solid pest control compositions typically are less prone to volatile dissemination of the active agent, and in some instances may be more readily and conveniently applied; for example, solid pest control compositions may be dropped from a helicopter or airplane or other elevated conveyance onto the surface of a large body of water somewhat more readily than can liquids. In addition, solid control agents are believed to be more able to penetrate a vegetative canopy when disseminated from an elevated conveyance.

When it is desired to form a solid composition for mosquitoes, a number of criteria are desirable. First, the solid pest control composition should be sufficiently durable to allow the control composition to be transported in bulk, such as by rail car or via bagged transport. Second, the solid composition, which generally will include a carrier and an active control agent, must be compatible with the pest target area environment; consequently, the carrier should be readily biodegradable. Third, the solid pest control composition should readily and quickly release the control agent when applied into a water column or when otherwise contacted by water, such as rain.

The prior art has provided numerous pest control compositions. For instance, U.S. Pat. No. 6,391,328 describes a process for treating organisms with a composition that includes a carrier, an active ingredient, and a coating. The carrier material is said to include silica, cellulose, metal oxides, clays, paper, infusorial earth, slag, hydrophobic materials, polymers such as polyvinyl alcohol and the like. Control of the release of rate of the active ingredient is said to be obtained via choice of coating material, which is said to be a fatty acid, alcohol or ester. Similar technology purportedly is disclosed in U.S. Pat. Nos. 6,387,386; 6,350,461; 6,346,262; 6,337,078; 6,335,027; 6,001,382; 5,902,596; 5,885,605; 5,858,386; 5,858,384; 5,846,553 and 5,698,210 (all by Levy to Lee County Mosquito Control District, Fort Meyers, Fla.).

Another pest control composition is disclosed in U.S. Pat. Nos. 5,824,328, 5,567,430, 5,983,390, and 4,418,534. In accordance with the purported teaching of these patents, the activation is provided in the form of a material that includes a super absorbent polymer and inert diluents.

U.S. Patent Publication 2007/0160637 discloses a pest control agent formed by providing a porous starch and an active control agent absorbed within the porous starch, and compressing the porous starch in the presence of heat to form discrete plural particles, including one or more binders, and one or more secondary absorbents/fillers. The can be prepared via pelletizing in a commercial pellet mill. The particles are sufficiently durable to withstand bulk transport, such as by rail car or bag shipment, and will release the control agent quickly upon contact with water, such that, for instance, the control agent may be released when the pest control agent is introduced to standing water.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Materials & Methods

Cell Culture and $Ca^{2+}$ Imaging.

For transient transfections, ORs were cloned into pCI (Promega) and transfected into Flp-In™ T-REx™293 cell lines (Invitrogen) with Fu GENE6 (Roche). For the creation of stable cell lines, a cell culture expression vector capable of expressing AgORco in conjunction with a conventional OR, pcDNA5/FRT/TO (Invitrogen) was modified to create two individual expression cassettes each under the control of a separate CMV/$TetO_2$ promoter and a BGH poly-adenylation signal. Cells (as above) were transfected with the modified pcDNA5 plasmid along with POG44 (a Flp recombinase expression plasmid) to facilitate site-specific recombination. Stable cell lines were selected using Hygromycin B (Invitrogen). Cells were maintained in DMEM (Invitrogen) supplemented with 10% Tetracycline-free FBS (HyClone) and 15 μg/ml Blasticidin. For fluorometric $Ca^{2+}$ measurements, stable lines expressing ORs of interest were seeded at 20,000 cells/well in black wall, poly-lysine coated 384-well cell culture plates (Greiner) and treated with 0.3 μg/μl tetracycline (Sigma) overnight to induce OR expression. Cells were dye-loaded with 1.8 μM Fluo-4 AM (Molecular Probes), 2.5 mM Probenecid (Molecular Probes) in assay buffer (20 mM HEPES, 1×HBSS) for 45 minutes at 37° C. in 5% $CO_2$ prior to each assay. $Ca^{2+}$ mobilization was assayed in an FDSS6000 (Hamamatsu). Baseline readings were taken for 20 s before automated addition of compound previously diluted in DMSO and assay buffer. Ratios were described as Maximum/Minimum response and each response was normalized to the maximum responder.

Chemicals.

VUAA1 was purchased from Sigma-Aldrich's Rare Chemical Library (CAS #525582-84-7). At time of print, VUAA1 was no longer available from Sigma-Aldrich. To ensure that observed activity was elicited from VUAA1, and not from a contaminant present in the mixture, the inventors performed preparative High Performance Liquid Chromatography (HPLC). Briefly, 20 mg of VUAA1 was dissolved in a 50/50 mixture of methanol and DMSO and HPLC was performed on a Phenomenex Luna 30×50 mm C18 prep column with 0.1% Trifluoracetic acid (TFA) in $H_2O$ coupled to an acetonitrile gradient. Appropriate fractions were pooled and passed over a TFA scavenger column (Polymer labs, StratoSpheres SPE PL-HCO3 MP-resin). The solvent was removed by rotary evaporation with a Biotage V10 Roto-vap, yielding white powder. VUAA1 was subsequently re-dissolved in DMSO and assayed as described.

Characterization of Chemical Materials.

$^1$H-NMR (400 MHz, DMSO-$_{d6}$) d 8.73 (d, J=1.8 Hz, 1H), 8.65 (dd, J=1.5, 4.8 Hz, 1H), 7.97 (dt, J=1.9, 8.0 Hz, 1H), 7.49 (dd, J=2.5, 8.3 Hz, 1H), 7.37 (d, J=8.4 Hz, 2H), 7.04 (d, J=8.4 HZ, 2H), 4.10 (s, 1H), 3.95 (q, J=7.2 Hz, 2H), 2.43 (q, J=7.6 Hz, 2H), 1.13 (t, J=8.0 Hz, 3H), 1.04 (t, J=8.0 Hz, 3H). $^{13}$C-NMR (400 MHz, DMSO-$_{d6}$) d 165.71, 152.92, 151.32, 150.95, 149.07, 139.35, 136.87, 136.33, 128.38, 124.34, 123.90, 119.58, 37.91, 27.97, 16.05, 15.42. HRMS (m/z) [M]$^+$ calculated for $C_{19}H_{22}N_5OS$, 368.1544 found 368.1545.

Patch-Clamp Recording in HEK Cells.

Currents from OR-expressing HEK293 cells were amplified with an Axopatch 200b Amplifier (Axon Instruments) and digitized through a Digidata 1322A (Axon Instruments). Electrophysiological data was recorded and analyzed using pCLAMP 10 (Axon Instruments). Electrodes were fabricated from quartz tubing (Sutter Instruments) and pulled to 4-6 MΩ for whole cell recording. Electrodes were filled with internal solution (120 mM KCl, 30 mM D-glucose, 10 mM HEPES, 2 mM $MgCl_2$, 1.1 mM EGTA, and 0.1 $CaCl_2$ (pH 7.35, 280 mOsm). External (bath) solution contained 130 mM NaCl, 34 mM D-glucose, 10 mM HEPES, 1.5 mM $CaCl_2$, 1.3 mM $KH_2PO_4$, and 0.5 $MgSO_4$ (pH 7.35, 300 mOsm). Compounds were diluted in external solution and locally perfused to the recording cell using Perfusion Pencil (Automate Scientific) and controlled by a ValveLink 8.2 controller (Automate Scientific). Whole cell recordings were sampled at 10 kHz and filtered at 5 kHz. Outside-out patches were obtained using 10-15MΩ electrodes pulled from standard glass capillaries (World Precision Instruments) and fire-polished with an MF-830 micro forge (Narishige). Single channel recordings were sampled at 20 kHz. Recordings were reduced to 1 kHz and low-pass filtered at 500 Hz for display and analysis using QuB (SUNY at Buffalo).

Single Sensillum Recordings.

Single sensillum recordings were performed on 4-7 day old, non-bloodfed *Anopheles gambiae* females maintained on 10% sucrose and a 12/12 light dark cycle. Legs, wings and antennae were removed from cold-anesthetized females that were then restrained on double-stick tape with thread. A glass reference electrode filled with Sensillar lymph ringers (SLR)(Xu, 2005) was placed in the eye and the recording electrode filled with DMSO or VUAA1 diluted in SLR was used to puncture sensilla at their base. Responses were recorded and digitized using a Syntech IDAC-4 and analyzed with AutoSpike software (Syntech). New glass recording pipettes were used for every recording. Data was sampled at 12 kHz.

Example 2: Results

Figure 3A:
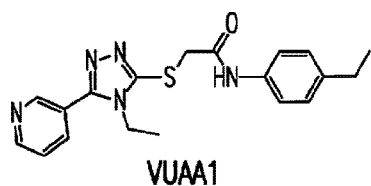
FIGS. 3A-F. VUAA1 evokes macroscopic currents in HEK293 cells expressing AgORco and its orthologs.
Figure 3B:
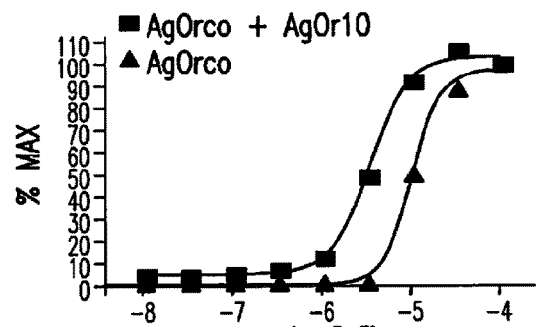

As part of an ongoing, cell based calcium imaging screen for novel small-molecule modulators of AgORs that might disrupt olfactory-driven mosquito behaviors (Rinker et at manuscript in preparation), the inventors identified a number of compounds that activated AgOR10+AgORco-expressing human embryonic kidney (HEK293) cells. One of these compounds (FIG. 3A), denoted here as VUAA1, elicited activity consistent with allosteric agonism and was pursued for its novel properties. The identity of VUAA1 was verified using high-resolution mass spectrometry (HRMS) as well as $^1$H and $^{13}$C NMR. When AgORco+AgOR10 cells were tested in a plate-based calcium imaging system, VUAA1 elicited concentration-dependent responses that were not seen in control cells (FIG. 3B). Upon further investigation, VUAA1 proved capable of activating other AgORco7+ AgOR10 cell lines as well (unpublished data). As AgORco was the common element among these functional responses, the inventors postulated that VUAA1 was a potential AgORco agonist.

Figure 3C:
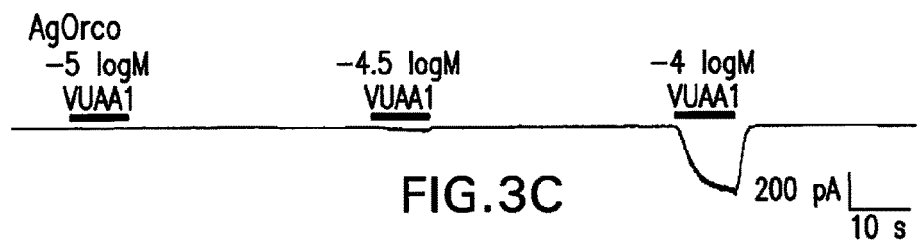
Figure 3D:
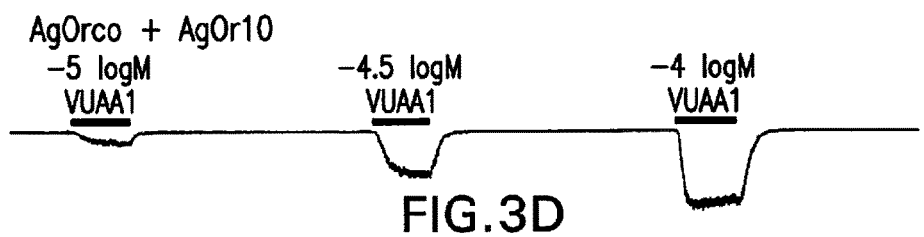
Figure 3E:
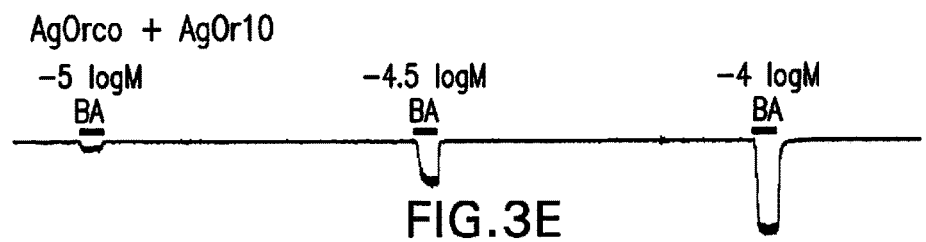
Figure 3F:
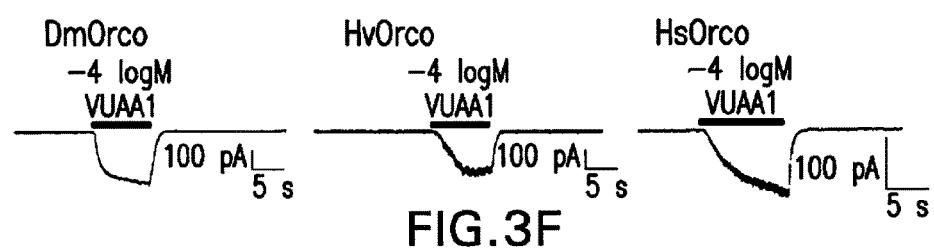

To test the hypothesis that VUAA1 directly agonized AgORco, whole-cell patch clamp responses were examined in AgORco+AgOR10 expressing cells as well HEK293 cells stably expressing AgORco alone. In these experiments, VUAA1 elicited concentration-dependent inward currents in both AgORco+AgOR10 and AgORco expressing cells (FIGS. 3D-E). The VUAA1-dependent currents in AgORco+AgOR10 cells resembled those resulting from application of benzaldehyde, an orthosteric agonist of AgOR10 (FIG. 3C) (Wang, 2010; Carey, 2010). AgORco+AgOR10 cells were more sensitive to VUAA1 than AgORco cells, producing inward currents at −5.0 log M, a concentration at which AgORco had no response. All currents induced by VUAA1 were AgORco-dependent; no responses were observed in control cells. To investigate the specificity of VUAA1 agonism, the inventors transiently transfected HEK cells with the AgORco orthologs of *Drosophila melanogaster* and *Heliothis virescens*, DmOR83b and HvOR2 respectively. In cells expressing either ortholog, VUAA1 elicited robust inward currents similar to AgORco-expressing cells (FIG. 3F). These results demonstrate that VUAA1 is a broad-spectrum 83b family agonist, capable of activating non-conventional ORs within and across multiple insect orders. This activity is consistent with their high sequence identities (76% to DmOR83b and 67% to HvOR2) and demonstrated functional overlap (Jones et al., 2005).

Figure 4A:
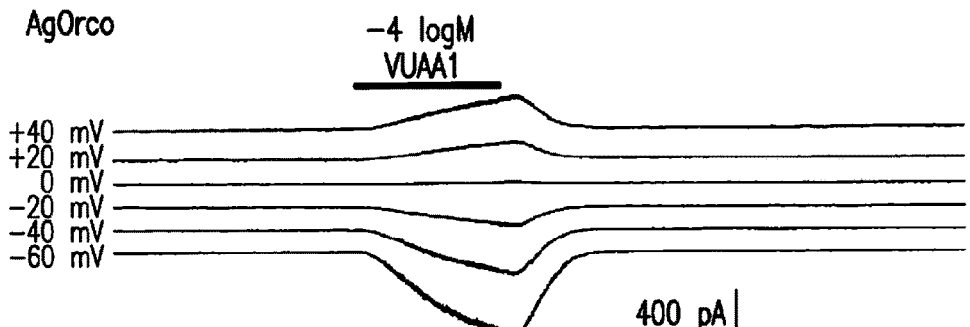
FIGS. 4A-D. Channel-like currents result from application of VUAA1 to cells expressing AgORco alone or in complex.
Figure 4B:
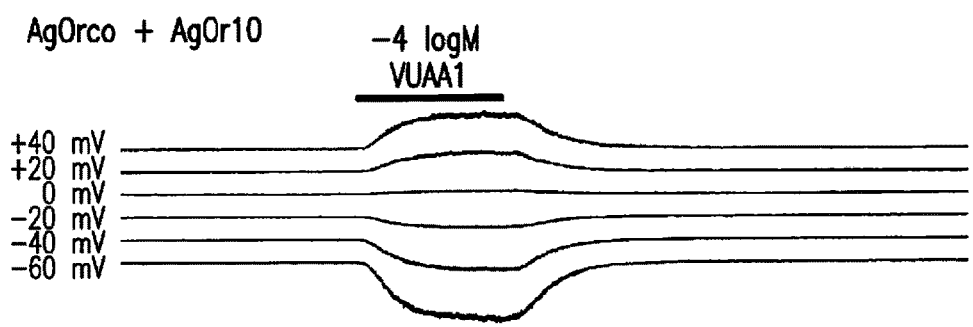
Figure 4C:
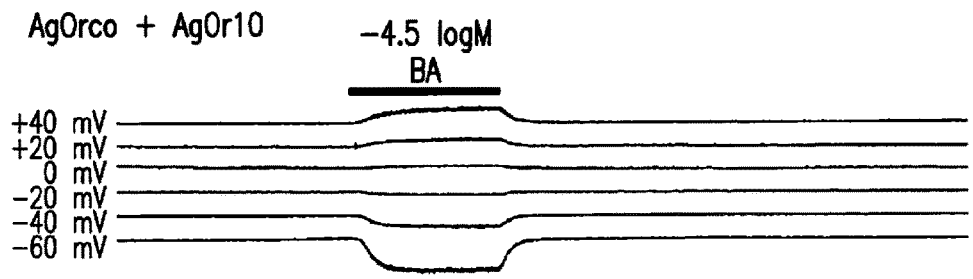
Figure 4D:
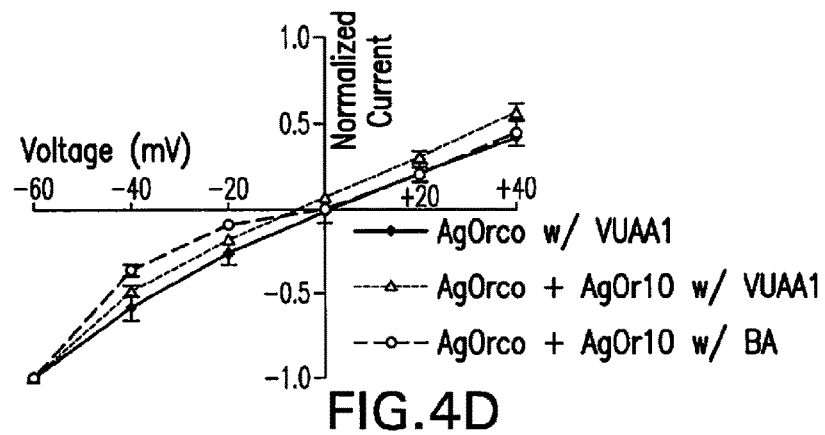

To further investigate the conductive properties of AgORco7, the inventors determined the current-voltage relationships of AgORco+AgOR10 complexes as well as AgORco on its own. Currents induced by VUAA-1 or benzaldehyde in AgORco+AgOR10-expressing cells, and those induced by VUAA-1 in AGORco cells, were all nearly symmetrical (FIGS. 4A-D and FIGS. 5A-D). The reversal potentials of AgORco+AgOR10 complexes were −2.9±1.4 mV (benzaldehyde) and −4.8±3.0 mV (VUAA1) while AgORco alone, in the presence of VUAA1 was +0.4±1.1 mV (mean±s.e.m. FIGS. 4A-C). These current-voltage relationships do not indicate any voltage-dependent gating, and the near-zero reversal potentials are consistent with previous reports of insect OR complexes that suggested non-selective cation conductance (Sato et al., 2008; Wicher et al., 2008). The inventors next examined whether VUAA1 responses could be attenuated by ruthenium red (RR), a promiscuous cation channel blocker previously found to block insect OR currents. Application of RR reduced the benzaldehyde and VUAA1-elicited currents of AgOrco+AgOR10 cells by 87.8±1.8% and 68.3±2.8%, respectively (FIGS. 5A-D) while RR reduced VUAA1 responses of AgORco cells by 79.4±4.0% (FIGS. 5C-D). In addition to demonstrating that AgORco+AgOR10 complexes, and AgORco alone act as functional, ligand-gated ion channels, these studies also show that VUAA1 elicits AgOR currents similar to those in response to odorants. To determine the broad-spectrum specificity of VUAA1, the inventors tested VUAA1 on another non-selective cation channel, transient receptor potential vanilloid receptor 1 (TRPV1) (Caterina, 1997; Bohlen, 2010). Capsaicin, but not VUAA1 elicited a robust response in these HEK cells (FIGS. 7A-F). These results demonstrate that VUAA1 is specific to 83b orthologs, and that VUAA1 is not a broad-spectrum activation of all cation channels The inventors next examined whether activation of AgORco involves second messenger-based signaling, which has been reported to contribute to insect olfactory signaling (Wicher, 2008). In these studies, which are consistent with a previously published report (Sato et al., 2008), two cyclic nucleotide analogs (8-Br cAMP and 8-Br cGMP) were unable to evoke whole-cell currents in AgORco or AgORco+AgOR10 cells, while in both instances OR function was validated by subsequent application of VUAA1 and benzaldehyde, respectively (FIGS. 8A-D). While the precise mechanism of signal transfer between a conventional OR and AgORco remains unknown, it is important to note that all channel properties are consistent between and within AgORco and AgOrco+AgOR10 complexes. Taken together, the data suggest that the channel properties of AgORco are not significantly altered when complexed with other AgORs and that the ionotropic conductance of AgORco is the principal signaling component of functional AgOR complexes.

Figure 5A:
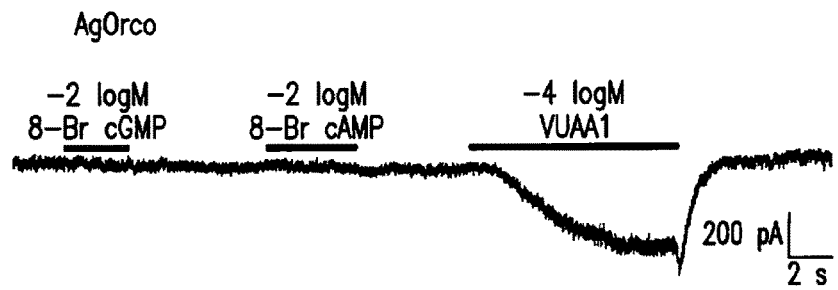
FIGS. 5A-D. AgORco is a functional channel and responds to VUAA1 in outside-out membrane patches.
Figure 5B:
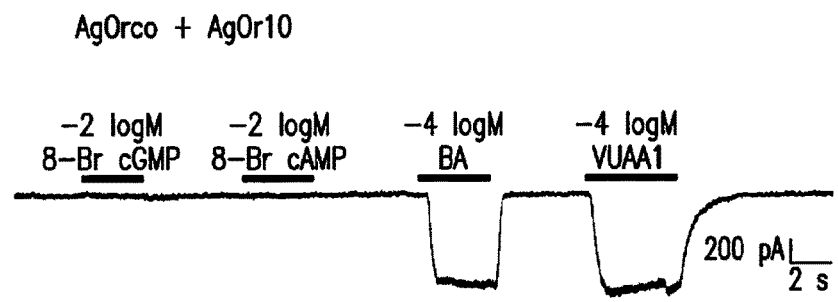
Figure 5C:
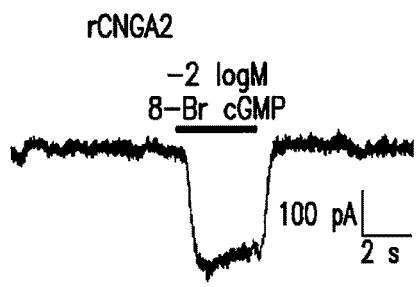
Figure 5D:
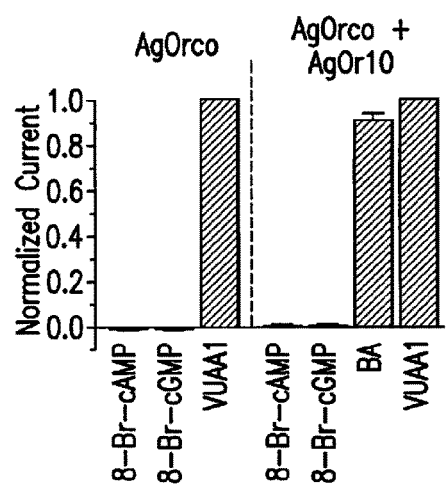
Figure 7A:
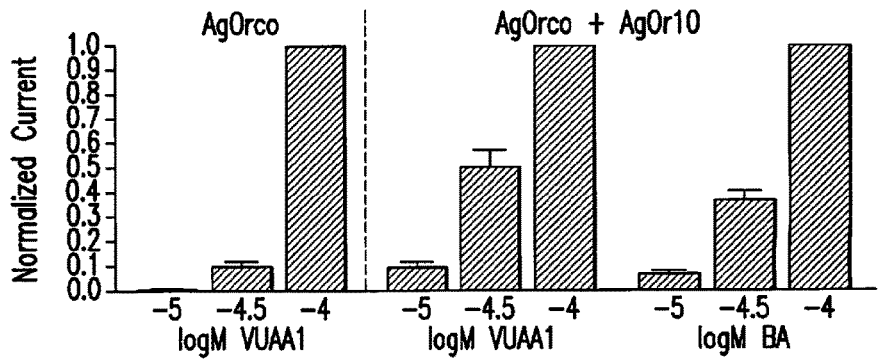
FIGS. 7A-F. VUAA1 and BA responses are OR specific.
Figure 7B:
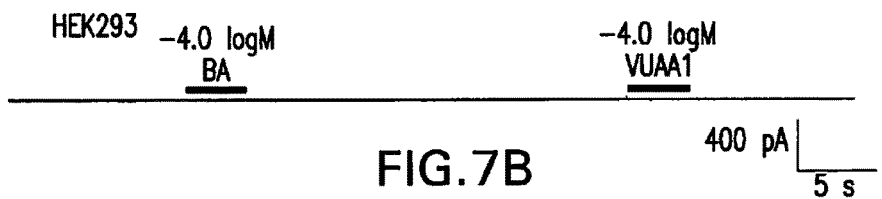
Figure 7C:
Figure 7D:
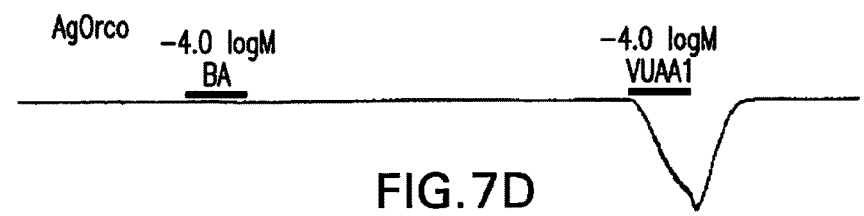
Figure 7E:
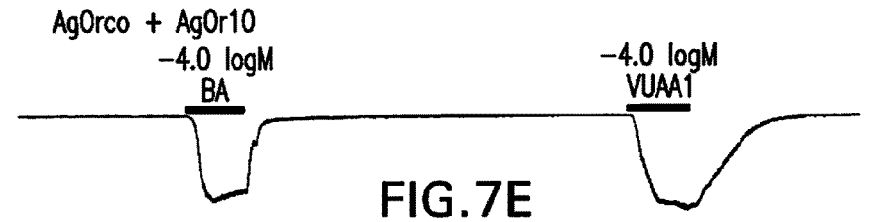
Figure 7F:
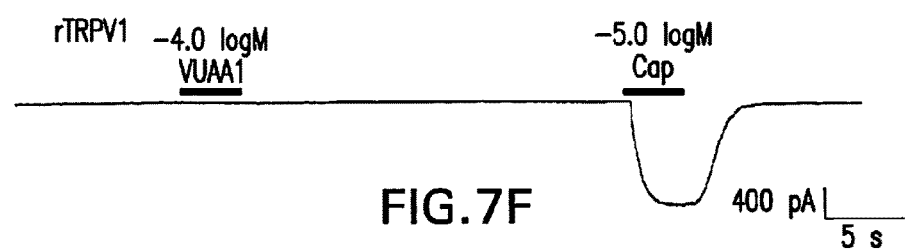
Figure 8A:
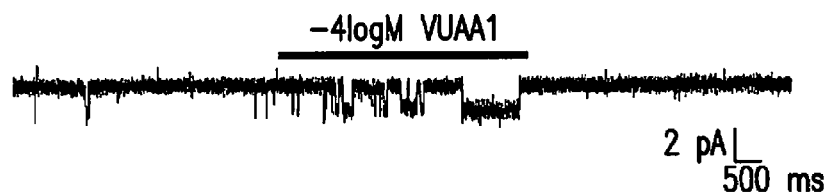
FIGS. 8A-D. 8-Br-cAMP and 8-Br-cGMP did not elicit currents in AgORco or AgORco+AgOR10 cells.
Figure 8B:
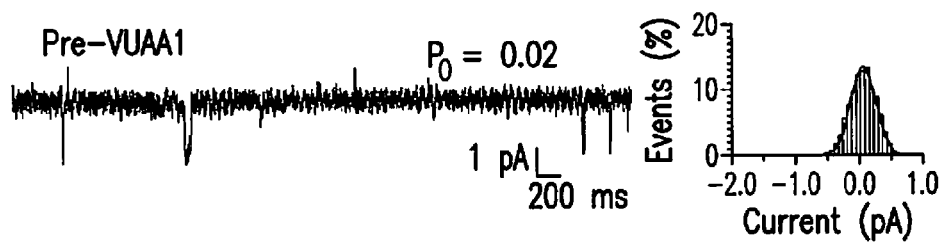
Figure 8C:
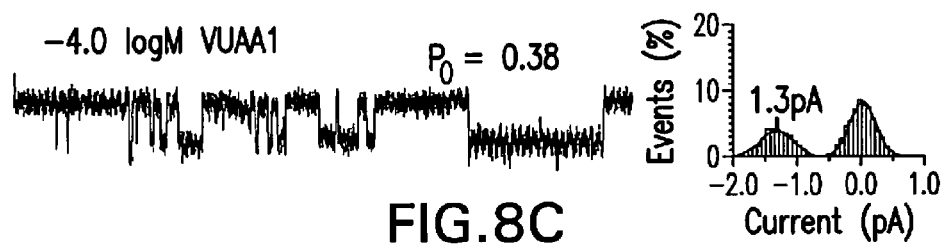
Figure 8D:
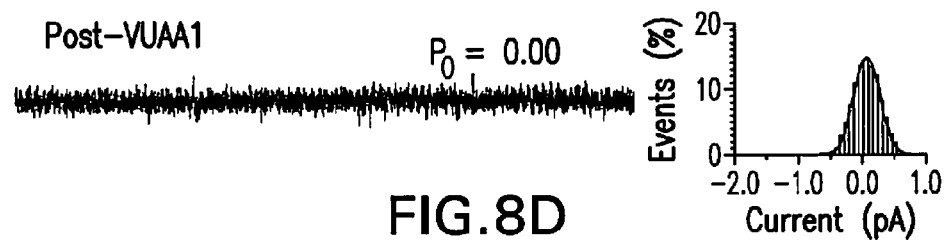

In the next set of studies, outside-out membrane patches were excised from AgORco-expressing cells to examine single-channel currents evoked by VUAA1 (FIG. 5A). Here, spontaneous channel opening was observed before VUAA1 stimulation, but with very low probability ($P_o$=0.02) (FIG. 5B). During a 5 s application of VUAA1 channel opening probability increased to $P_o$=0.38 (FIG. 5C). Subsequent to agonist washout, channel opening probability decreased to 0.00 (FIG. 5D). The average unitary current of AgORco was 1.3±0.3 pA (mean±st. dev.) (FIG. 5C, inset) which is consistent with earlier single-channel studies of insect ORs (Sato et al., 2008). Taken together, these data support our hypothesis that VUAA1 can agonize AgORco in the absence of other intracellular components and provide additional support for the role of VUAA1 as a direct agonist of AgORco and other OR83b family members.

The inventors next performed single unit, extracellular electrophysiological recordings on adult female *An. gambiae* to determine whether VUAA1 could activate AgORco-expressing odorant receptor neurons (ORNs) in vivo. ORNs, which express AgORco and a conventional OR are enclosed within the hair-like sensilla present on olfactory tissues. The highly stereotypic capitate peg (Cp) sensilla, which are found on the maxillary palp, contain two ORco expressing neurons (CpB and CpC) as well as a $CO_2$ sensitive neuron (CpA), which does not express AgORco (Lu et al., 2007). CpA is clearly distinguished from CpB/C by its large action potential amplitude. The action potential amplitudes of CpB and CpC are much smaller and in some preparations indistinguishable from each other; as a result, the spike activity of CpB and CpC neurons were binned for data analysis. Accordingly, the inventors would expect that if VUAA1 is a specific AgORco agonist, it should selectively increase the spike frequency of the CpB and CpC neurons but have no effect on CpA responses.

Due to its relatively high molecular weight, volatile delivery of VUAA1 was not feasible. As a result, VUAA1 was directly added to each sensillum via the glass-recording electrode where VUAA1 increased the spike frequency of CpB/C neurons in a dose-dependent manner; vehicle alone had no effect (FIGS. 6A, B, D). Differential CpB/C spike activity was observed immediately after puncturing each sensillum, suggesting millisecond compound diffusion rates into the sensillum (FIGS. 6A, B, D). At the completion of each assay, a $CO_2$ pulse was delivered to the sensillum to test whether VUAA1 affected the CpA neuron; in contrast to the responsiveness of the AgORco-expressing CpB/C neurons, CpA activity was unchanged in the presence of vehicle and/or VUAA1 (FIGS. 6A, B, D). These data demonstrate that VUAA1 can specifically activate AgORco-expressing neurons in vivo. Moreover, VUAA1's ability to activate AgORco-expressing cells in vivo demonstrates that AgORco is an accessible biological target, which is not directly obscured by other proteins or cofactors involved in olfactory signal transduction. As such, VUAA1-mediated modulation serves as a proof-of-concept demonstration that AgORco is a viable target for the development of behaviorally disruptive olfactory compounds (BDOCs) that could foster malaria reduction programs.

While the inventors cannot rule out an eventual identification, there is currently no evidence to support the existence of naturally-occurring AgORco ligands, which suggests that AgORco lacks a typical orthosteric binding site common to other ligand-gated ion channels. Without a more advanced structural analysis of AgORco, it is difficult to postulate as to the mechanism of VUAA1 gating, and whether it is acts in a manner akin to canonical OR-dependent activation of the heteromeric OR complex. However, it is clear that AgORco is ionotropic, ligand-gated ion channel.

In order to address whether VUAA1 as a non-volatile could also evoke behavioral responses from *An. gambiae*, the inventors tested behavioral responses to VUAA1 on individual larval stage mosquitoes by adaptation of an olfactory based bioassay recently developed at Vanderbilt (described in Liu et al., 2010). These methods are non-invasive, and easily executed using a fully automated setup with an Ethovision® camera/software system (Noldus Information Technology to quantify the overall movement of mosquito larvae in response to uniform concentrations of chemicals. In these assays, increased overall movement can be interpreted as an aversive response (akin to agitation) that are consistent with those evoked by commercially available insect repellents such as DEET.

Figure 9:
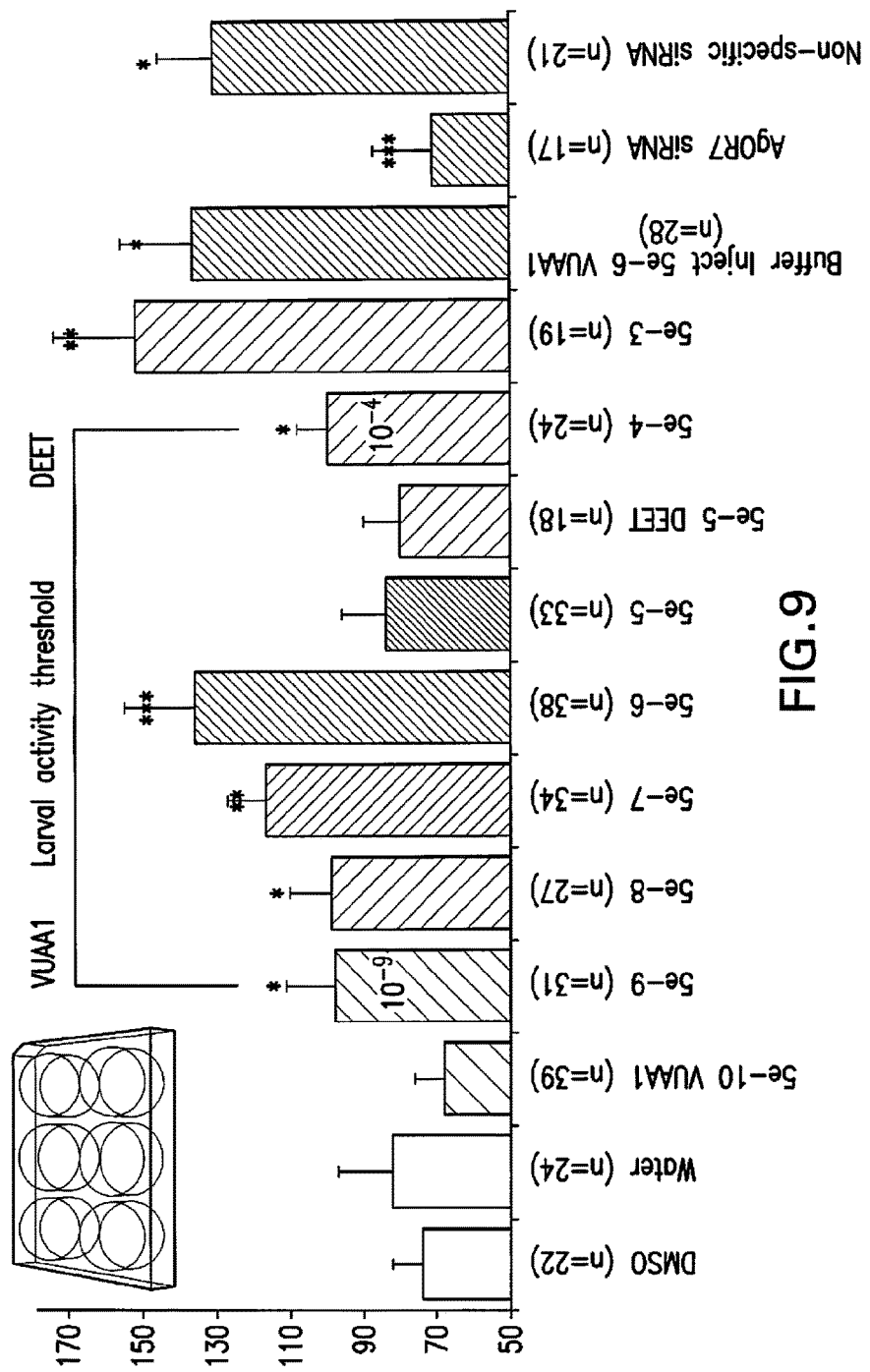
FIG. 9. VUAA1's larval activity threshold relative to DEET is 5 orders of magnitude lower and AgORco dependent. Larval activity in *An. gambiae* over 5 minutes monitored in 6-well culture plates using Ethovision (Noldus) software. Larval responses to VUAA1 (third through eighth from left) are significantly higher than those to DEET (ninth through eleventh from left). Gene silencing studies (twelfth through fourteenth from left) demonstrate that larval responses to VUAA1 are AgORco-dependent in keeping with VUAA1's mode of action.

With regard to VUAA1, these studies (FIG. 9) indicate that VUAA1 evokes robust responses from *An. gambiae* larvae that are consistent with repellency and the threshold of larval responses to VUAA1 (third through eighth bars from left) are 5 orders of magnitude lower than those to DEET (ninth through eleventh bars from left bars). Furthermore, gene-silencing studies using siRNAs directed against AgORco demonstrate that larval sensitivity to VUAA are dependent upon AgORco expression. Here larvae treated with AgOrco siRNAs (which reduce AgORco mRNA levels 40-fold) no longer respond to VUAA1 stimuli while larvae receiving mock or non-specific siRNA control injection retain their high sensitivity to VUAA1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. REFERENCES

The following references, to the extent that they provide exemplary procedural or other details supplementary to those set forth herein, are specifically incorporated herein by reference:

U.S. Pat. No. 2,798,053
U.S. Pat. No. 3,755,560
U.S. Pat. No. 4,418,534
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,567,430
U.S. Pat. No. 5,698,210
U.S. Pat. No. 5,824,328
U.S. Pat. No. 5,846,553
U.S. Pat. No. 5,858,384
U.S. Pat. No. 5,858,386
U.S. Pat. No. 5,885,605
U.S. Pat. No. 5,902,596
U.S. Pat. No. 5,983,390
U.S. Pat. No. 6,001,382
U.S. Pat. No. 6,335,027
U.S. Pat. No. 6,337,078
U.S. Pat. No. 6,346,262
U.S. Pat. No. 6,350,461
U.S. Pat. No. 6,387,386
U.S. Pat. No. 6,391,328
U.S. Pat. No. 7,090,147
U.S. Pat. No. 7,306,167
U.S. Patent Publn. 2006/0260183
U.S. Patent Publn. 2007/0160637
Acree et al., *Science*, 161:1346-1347, 1968.
Antonny et al., *J. Biol. Chem.*, 268:2393-2402, 1993.
Baumann et al., *Embo. J.*, 13:5040-5050, 1994.
Benton et al., *Cell*, 136:149-162, 2009.
Benton et al., *PLoS Biol.*, 4:e20, 2006.
Bernier et al., *Anal. Chem.*, 71:1-7, 1999.
Boekhoff et al., *J. Comparative Physiol. B*, 160:99-103, 1990.
Bohbot et al., *Insect. Mol. Biol.*, 16:525-537, 2007.
Brady et al., *Ann. Trop. Med. Parasitol.*, 91:S121-122, 1997.
Breer et al., *Nature*, 345:65-68, 1990.

Carnevale et al., *Bull. World Health Organ.*, 56:147-154, 1978.
Clyne et al., *Neuron.*, 22:327-338, 1999.
Clyne et al., *Science*, 287:1830-1834, 2000.
Cork and Park, *Med. Vet. Entomol.*, 10:269-276, 1996.
CTFA Cosmetic Ingredient Handbook, Vol. 3, p. 3187-3192
Curtis, *Parasitology Today*, 11:316-318, 1986.
De Jong and Knols, *Acta Trop.*, 59:333-335, 1995.
De Jong and Knols, *Experientia*, 51:80-84, 1995.
Dekker et al., *J. Med. Entomol.*, 38:868-871, 2001a.
Dekker et al., *Physiol. Entomol.*, 26:124-134, 2001b.
Dobritsa et al., *Neuron.*, 37:827-841, 2003.
Eiras and Jepson, *Bull. Entomol. Res.*, 81:151-160, 1991.
Elmore and Smith, *Insect Biochem. Mol. Biol.*, 31:791-798, 2001.
Engsontia et al., *Insect Biochem. Mol. Biol.*, 38:387-397, 2008.
Fox et al., *Proc. Natl. Acad. Sci. USA*, 98:14693-14697, 2001.
Gao and Chess, *Genomics*, 60:31-39, 1999.
Gilles, *Bull. Entomol. Res.*, 70:525-532, 1980.
Goldman et al., *Neuron.*, 45:661-666, 2005.
Hallem and Carlson, *Cell*, 125:143-160, 2006.
Hallem et al., *Cell*, 117:965-979, 2004a.
Hallem et al., *Nature*, 427:212-213, 2004b.
Hildebrand and Shepherd, *Annu. Rev. Neurosci.*, 20:595-631, 1997.
Hill et al., *Science*, 298:176-178, 2002.
Holt et al., *Science*, 298:129-149, 2002.
Jones et al., *Curr. Biol.*, 15:R119-R121, 2005.
Jones et al., *Nature*, 445:86-90, 2007.
Kellogg, *J. Insect. Physiol.*, 16:99-108, 1970.
Kim et al., *Bioinformatics*, 16:767-775, 2000.
Krieger and Breer, *Science*, 286:720-723, 1999.
Krieger et al., *Eur. J. Neurosci.*, 16:619-628, 2002.
Krieger et al., *Insect. Biochem. Mol. Biol.*, 29:255-267, 1999.
Krieger et al., *J. Comp. Physiol. A Neuroethol. Sens. Neural. Behav. Physiol.*, 189:519-526, 2003.
Krotoszynski et al., *J. Chromotographic Sci.*, 15:239-244, 1977.
Kwon et al., *Proc. Natl. Acad. Sci. USA*, 104:3574-3578, 2007.
Labows Jr., *Perfumer & Flavorist*, 4:12-17, 1979.
Larsson et al., *Neuron.*, 43:703-714, 2004.
Laue et al., *Cell Tissue Res.*, 288:149-158, 1997.
Lindsay et al., *J. Med. Entomol.*, 30:308-373, 1993.
Lu et al., *Curr. Biol.*, 17:1533-1544, 2007.
Liu et al., *PLoS Biology* 8(8): e1000467, 2010.
Lundin et al., *FEBS Lett.*, 581(29):5601-5604, 2007.
Mboera and Takken, Rev. *Med. Vet. Entomol.*, 85:355-368, 1997.
McCutcheon's, Detergents and Emulsifiers, North American Edition, 1986.
Meijerink and van Loon, *J. Insect Physiol.*, 45:365-373, 1999.
Meijerink et al., *J. Insect Physiol.*, 47:455-464, 2001.
Merrill et al., *Insect Molecul. Biol.*, 12:641-650, 2003.
Merrill et al., *J. Neurobiol.*, 63:15-28, 2005.
Merrill et al., *Proc. Natl. Acad. Sci. USA*, 99:1633-1638, 2002.
Mombaerts, *Annu. Rev. Neurosci.*, 22:487-509, 1999.
Muirhead-Thomson, *Brit. Med. J.*, I:1114-1117, 1951.
Pelosi and Maida, *Comp. Biochem. Physiol. B Biochem. Mol. Biol.*, 111:503-514, 1995.
Pitts et al., *Proc. Natl. Acad. Sci. USA*, 101:5058-5063, 2004.
Qiu et al., *Chem. Senses*, 31:845-863, 2006b.
Qiu et al., *Med. Vet. Entomol.*, 20:280-287, 2006a.
Remington's Pharmaceutical Sciences, 18th Ed. Mack Printing Company, 1289-1329, 1990.
Robertson and Wanner, *Genome Res.*, 16:1395-1403, 2006.
Robertson et al., *Proc. Natl. Acad. Sci. USA*, 100(2):14537-14542, 2003.
Rutzler et al., *J. Comp. Neurol.*, 499:533-545, 2006.
Sato et al., *Nature*, 452(7190):1002-1006, 2008.
Schreck et al., *J. Am. Mosq. Control Assoc.*, 6:406-410, 1990.
Scott et al., *Cell*, 104:661-673, 2001.
Smith, *Neuron.*, 22:203-204, 1999.
Stengl, *J. Comp. Physiol. [A]*, 174:187-194, 1994.
Storkuhl and Kettler, *Proc. Natl. Acad. Sci. USA*, 98:9381-9385, 2001.
Suh et al., *Curr. Biol.*, 17:905-908, 2007.
Takken and Knols, *Annu. Rev. Entomol.*, 44:131-157, 1999.
Takken et al., *J. Insect Behavior*, 10:395-407, 1997.
Takken, *Insect Sci. Applns.*, 12:287-295, 1991.
Thomas, *Brit. Med. J.*, 2:1402, 1951.
Vosshall et al., *Cell*, 102:147-159, 2000.
Vosshall et al., *Cell*, 96:725-736, 1999.
Vosshall, *Chem. Senses*, 26:207-213, 2001.
Wetzel et al., *Proc. Natl. Acad. Sci. USA*, 98:9377-9380, 2001.
Wicher et al., *Nature*, 452(7190):1007-1011, 2008.
Wistrand et al., *Protein Sci.*, 15:509-521, 2006.
Xia et al., *Proc. Natl. Acad. Sci. USA*, 105:6433-6438, 2008.
Zwiebel and Takken, *Insect Biochem. Molec. Biol.*, 34:645-652, 2004.

What is claimed is:

1. A composition comprising a compound:

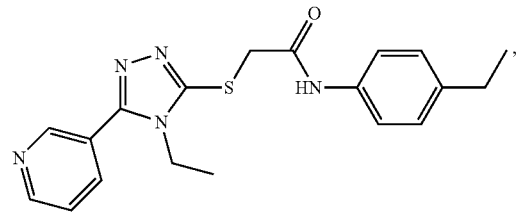 [SMILES: CCc1ccc(NC(=O)CSc2nnc(-c3cccnc3)n2CC)cc1]

or a salt thereof, and
one or more aerosolizers, film formers, ester-containing solvents, gelling agents, skin-conditioning agents, emollients, antioxidants, structuring agents, emulsifiers, silicone-containing compounds, essential oils, thickening agents, and/or vehicles.

2. The composition of claim 1, comprising one or more aerosolizers, gelling agents, emollients, emulsifiers, essential oils, and/or vehicles.

3. The composition of claim 1, wherein the compound is present as:

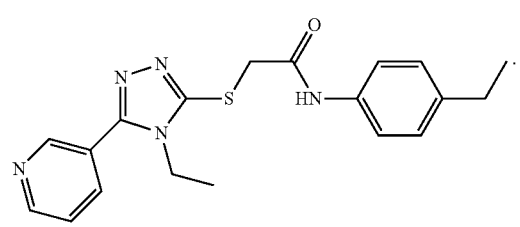

4. The composition of claim 1, wherein the compound is present as a salt.

5. The composition of claim 1, comprising one or more film formers, ester-containing solvents, skin-conditioning agents, antioxidants, structuring agents, emulsifiers, silicone-containing compounds, and/or thickening agents.

6. The composition of claim 1, comprising one or more aerosolizers.

7. The composition of claim 1, comprising one or more gelling agents.

8. The composition of claim 1, comprising one or more emollients.

9. The composition of claim 1, comprising one or more emulsifiers.

10. The composition of claim 1, comprising one or more essential oils.

11. An article comprising a compound:

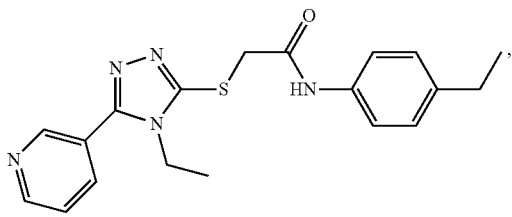 [SMILES: CCc1ccc(NC(=O)CSc2nnc(-c3cccnc3)n2CC)cc1]

or a salt thereof, wherein the article is selected from a misting system, bait, a pellet, fabric, clothing, shelter, bedding, netting, and a water soluble tablet.

12. The article of claim 11, comprising fabric, clothing, shelter, bedding, and/or netting.

13. The article of claim 11, wherein the compound is present as:

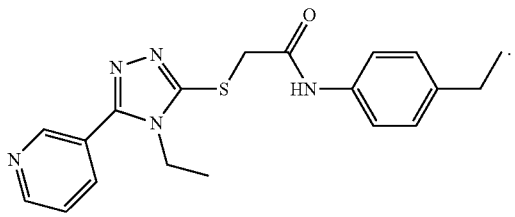 [SMILES: CCc1ccc(NC(=O)CSc2nnc(-c3cccnc3)n2CC)cc1]

14. The article of claim 11, wherein the compound is present as a salt.

15. The article of claim 11, selected from misting system, bait, pellet, and water soluble tablet.

16. The article of claim 11, comprising fabric.

17. The article of claim 11, comprising clothing.

18. The article of claim 11, comprising shelter.

19. The article of claim 11, comprising bedding.

20. The article of claim 11, comprising netting.

* * * * *